US012217539B2

United States Patent
Morishita

(10) Patent No.: US 12,217,539 B2
(45) Date of Patent: *Feb. 4, 2025

(54) ESTIMATION DEVICE, ESTIMATION METHOD, AND STORAGE MEDIUM

(71) Applicant: NEC Corporation, Tokyo (JP)

(72) Inventor: Yusuke Morishita, Tokyo (JP)

(73) Assignee: NEC CORPORATION, Tokyo (JP)

( * ) Notice: Subject to any disclaimer, the term of this patent is extended or adjusted under 35 U.S.C. 154(b) by 148 days.

This patent is subject to a terminal disclaimer.

(21) Appl. No.: 17/680,853

(22) Filed: Feb. 25, 2022

(65) Prior Publication Data

US 2022/0180556 A1 Jun. 9, 2022

Related U.S. Application Data

(63) Continuation of application No. 17/278,500, filed as application No. PCT/JP2018/035785 on Sep. 26, 2018.

(51) Int. Cl.
 *G06V 40/16* (2022.01)
 *G06T 7/73* (2017.01)
 (Continued)

(52) U.S. Cl.
 CPC .............. *G06V 40/171* (2022.01); *G06T 7/73* (2017.01); *G06V 10/25* (2022.01); *G06V 40/168* (2022.01);
 (Continued)

(58) Field of Classification Search
 CPC ..... H04L 27/01; H04L 25/061; H04L 7/0079; H04L 27/0002; H04B 17/21; H04B 1/06; H04B 1/16
 See application file for complete search history.

(56) References Cited

U.S. PATENT DOCUMENTS 6,606,397 B1 8/2003 Yamamoto
8,265,410 B1 9/2012 Konoplev
(Continued)

FOREIGN PATENT DOCUMENTS

EP 2042079 A1 4/2009
JP 2000-339457 A 12/2000
(Continued)

OTHER PUBLICATIONS

JP Office Action for JP Application No. 2020-547686, mailed on Jun. 14, 2022 with English Translation.
(Continued)

*Primary Examiner* — Amara Abdi

(57) ABSTRACT

An estimation device according to one aspect of the present disclosure includes: at least one memory storing a set of instructions; and at least one processor configured to execute the set of instructions to: generate a plurality of extraction regions by adding a perturbation to an extraction region of a partial image determined based on positions of feature points extracted from a face image; estimate a plurality of directions of at least one of a face and a line of sight and a reliability of each of the plurality of directions based on a plurality of partial images in the plurality of extraction regions of the face image; and calculate an integrated direction obtained by integrating the plurality of directions based on the estimated reliability.

18 Claims, 7 Drawing Sheets

(51) Int. Cl.
  *G06V 10/25*  (2022.01)
  *G06V 40/18*  (2022.01)

(52) U.S. Cl.
  CPC .. *G06V 40/197* (2022.01); *G06T 2207/30201* (2013.01)

(56) References Cited

U.S. PATENT DOCUMENTS

| | | | |
|---|---|---|---|
| 9,858,473 B2* | 1/2018 | Izumi | G06V 40/171 |
| 2008/0192990 A1 | 8/2008 | Kozakaya | |
| 2009/0060291 A1 | 3/2009 | Ohtani et al. | |
| 2009/0304232 A1 | 12/2009 | Tsukizawa | |
| 2011/0158542 A1 | 6/2011 | Kato et al. | |
| 2011/0249868 A1 | 10/2011 | Tsukizawa et al. | |
| 2012/0033853 A1 | 2/2012 | Kaneda et al. | |
| 2012/0189160 A1* | 7/2012 | Kaneda | G06V 40/19 348/207.99 |
| 2012/0201468 A1 | 8/2012 | Oami et al. | |
| 2013/0022277 A1 | 1/2013 | Morishita | |
| 2015/0117771 A1 | 4/2015 | Sasaki | |
| 2015/0172553 A1 | 6/2015 | Nonaka et al. | |
| 2015/0254501 A1* | 9/2015 | Yamanashi | H04N 7/18 348/78 |
| 2015/0339757 A1* | 11/2015 | Aarabi | G06Q 30/0631 705/26.7 |
| 2017/0243054 A1 | 8/2017 | Lee et al. | |
| 2017/0293354 A1 | 10/2017 | Lu et al. | |
| 2019/0156522 A1* | 5/2019 | Sugaya | G06T 11/001 |
| 2019/0163966 A1 | 5/2019 | Moriya | |
| 2019/0279347 A1 | 9/2019 | Hayasaka | |
| 2020/0058136 A1* | 2/2020 | Morishita | G06T 7/70 |
| 2020/0242336 A1* | 7/2020 | Boic | G06V 40/168 |
| 2021/0192184 A1* | 6/2021 | Zeng | G06V 40/166 |
| 2021/0327058 A1* | 10/2021 | Hu | G06V 40/168 |

FOREIGN PATENT DOCUMENTS

| | | |
|---|---|---|
| JP | 2008-210239 A | 9/2008 |
| JP | 2009-059257 A | 3/2009 |
| JP | 2010-211613 A | 9/2010 |
| JP | 2011-138388 A | 7/2011 |
| JP | 4829141 B2 | 9/2011 |
| JP | 2012-037934 A | 2/2012 |
| JP | 2012-038106 A | 2/2012 |
| JP | 2014-210076 A | 11/2014 |
| JP | 5772821 B2 | 7/2015 |
| WO | 2008/007781 A1 | 1/2008 |
| WO | 2010/035472 A1 | 4/2010 |
| WO | 2011/046128 A1 | 4/2011 |
| WO | 2016/093459 A1 | 6/2016 |
| WO | 2018/008575 A1 | 1/2018 |
| WO | 2018/078857 A1 | 5/2018 |

OTHER PUBLICATIONS

International Search Report for PCT Application No. PCT/JP2018/035785, mailed on Dec. 4, 2018.
English translation of Written opinion for PCT Application No. PCT/JP2018/035785, mailed on Dec. 4, 2018.
Jian-Gang Wang, et al., "Eye Gaze Estimation from a Single Image of One Eye," Proceedings of Ninth IEEE International Conference on Computer Vision (ICCV 2003).
Rajeev Ranjan et al., "HyperFace: A Deep Multi-task Learning Framework for Face Detection, Landmark Localization, Pose Estimation, and Gender Recognition," IEEE Transactions on Pattern Analysis and Machine Intelligence, vol. 41, No. 1 Jan. 2017, pp. 121-135.
Xucong Zhang et al., "Appearance-Based Gaze Estimation in the Wild", Proceedings IEEE CVPR 2015, pp. 4511-4520, 2015.
Extended European Search Report for EP Application No. 18935616.5 dated on Aug. 11, 2021.
US Office Action for U.S. Appl. No. 17/278,500, mailed on Nov. 2, 2023.
US Office Action for U.S. Appl. No. 17/680,844, mailed on Dec. 7, 2023.
U.S. Office Action for U.S. Appl. No. 17/278,500, mailed on Aug. 15, 2024.
U.S. Office Action for U.S. Appl. No. 17/278,500, mailed on Dec. 6, 2024.

* cited by examiner

ESTIMATION DEVICE, ESTIMATION METHOD, AND STORAGE MEDIUM

The present application is a Continuation application of Ser. No. 17/278,500 filed on Mar. 22, 2021, which is a National Stage Entry of PCT/JP2018/035785 filed on Sep. 26, 2018, the contents of all of which are incorporated herein by reference, in their entirety.

TECHNICAL FIELD

The present disclosure relates to a technique for estimating a direction, and particularly, to a technique for estimating a direction of a line of sight or a face of a person included in an image.

BACKGROUND ART

Directions of a line of sight (that is, direction at which eyes look) and a face of a person may be important clues to analyze a behavior and an intention of the person. For example, an object or an event at which the person looks can be specified from the line of sight of the person.

An intended line of sight can be specified from a difference between the directions of the line of sight and the face orientation obtained by measuring the line of sight and the face orientation of the person. Specifically, the face orientation and the line of sight of the person are generally directed in the same direction in many cases. However, in a case where the line of sight and the face orientation of the person are different from each other, for example, in a case where the face is oriented to the right and the line of sight is directed to the left, it is considered that the person tries to look at a target while hiding the direction of the line of sight from others. The others can easily recognize the face orientation of the person. However, it is not possible for the others to recognize the direction of the line of sight unless the others approach the person to some extent. In this way, whether the person looks at the target with some intention can be specified by measuring the line of sight and the face orientation of the person.

A technique for estimating a line of sight and a face orientation of a person, particularly, a technique for estimating the line of sight and the face orientation of the person using an image including a face of the person (hereinafter, referred to as "face image") are disclosed in the documents described below.

Techniques for estimating the line of sight on the basis of the face image are described, for example, in PTLs 1 to 3 and NPLs 1 and 2. PTL 1 discloses a method for estimating a line of sight using feature points included in a face image (image feature point) (feature-based methods). NPL 1 discloses a method for estimating a line of sight from a face image including only one eye.

PTL 2 and NPL 2 disclose examples of "estimation of a line of sight based on an appearance" (appearance-based gaze estimation). For example, in PTL 2, a relationship between a face and a line of sight is learned by performing deep learning based on a Convolutional neural network (CNN) model using a given data set of a face image.

A technique for estimating a face orientation on the basis of a face image is described, for example, in NPL 3. NPL 3 discloses a method for simultaneously estimating a position of the face and a position of a part of the face, an orientation of the face, or the like by performing deep learning based on the CNN model.

PTL 4 discloses a device that estimates a line of sight direction on the basis of a difference between the center position of the face calculated on the basis of three-dimensional positions of parts of the face and the center position of the pupil.

PTL 5 discloses a device that detects a direction of a line of sight on the basis of an outline of the face and positions of the eyes.

PTL 6 discloses a device that estimates a direction recognized as the front by a vehicle driver on the basis of a time-series change in the estimated line of sight and corrects the direction of the line of sight on the basis of the estimated direction.

PTL 7 discloses a device that estimates an eye region on the basis of a result of detecting the nostril and determines an eye opened/closed state.

PTL 8 discloses a device that determines a face orientation by projecting a vector indicating coordinates of the detected feature points on each of partial spaces generated for a plurality of face orientations and integrating the directions determined for the respective partial spaces.

PTL 9 discloses a device that estimates a direction of a line of sight on the basis of a feature amount of an eye region and a reliability of each of both eyes according to a detected face orientation.

CITATION LIST

Patent Literature

[PTL 1] JP 4829141 B2
[PTL 2] JP 2009-059257 A
[PTL 3] JP 5772821 B2
[PTL 4] WO 2008/007781 A
[PTL 5] JP 2014-210076 A
[PTL 6] JP 2008-210239 A
[PTL 7] JP 2000-339457 A
[PTL 8] JP 2011-138388 A
[PTL 9] JP 2012-037934 A

Non Patent Literature

[NPL 1] J. Wang, E. Sung, and R. Venkateswarlu (2003), "Eye Gaze Estimation from a Single Image of One Eye," Proc. IEEE ICCV 2003, pp. I-136-143.
[NPL 2] X. Zhang, Y. Sugano, M. Fritz and A. Bulling (2015), "Appearance-Based Gaze Estimation in the Wild," Proc. IEEE CVPR 2015, pp. 4511-4520.
[NPL 3] R. Ranjan, V. M. Patel, R. Chellappa (2017), "HyperFace: A Deep Multi-task Learning Framework for Face Detection, Landmark Localization, Pose Estimation, and Gender Recognition," IEEE Transactions on Pattern Analysis and Machine Intelligence.

SUMMARY OF INVENTION

Technical Problem

In the related art described above, the line of sight and the face orientation are estimated from a single image. Therefore, in a case where the image that is an estimation target is not suitable for estimation because of imaging conditions and shielding, it is not possible to perform accurate estimation. Even if an error occurs in the estimation result, it is not possible to correct the error. For example, the technique disclosed in NPL 2 estimates a line of sight from a single input face image. Therefore, in a case where a state of the image is poor, it is not possible to accurately obtain positions of the face and the eyes. A case where the state of the image is poor includes, for example, a case where an entire image is dark due to a poor lighting condition, or in a case where the face is shadowed. A case where the state of the image is poor includes, for example, a case where the face or the eye is not clearly reflected in the image or a case where a part of the eye or the face is shielded by another object. If it is not possible to accuracy obtain the positions of the face and the eyes, it is not possible to accuracy extract the eye regions used to estimate the line of sight. As a result, the estimation of the line of sight may fail.

Even if the eye regions can be accuracy extracted, in a case where the vicinity of the eyes is dark or in a case where the eyes are shielded, sufficient information to estimate the line of sight is not included in the image of the eye region. Therefore, there is a case where the estimation of the line of sight fails.

In the technique disclosed in NPL 3, the positions of the face and the parts of the face are detected from the single input image, and the face orientation is estimated. Therefore, in a case similar to the above case, there is a case where the estimation of the face orientation fails for the similar reasons.

That is, according to the technique for estimating the direction of the face or the like from the single image disclosed in the above-described document, for example, in a case where the state of the image is not suitable for estimation of the feature points of the face, it is difficult to estimate the line of sight and the face orientation with high accuracy.

An object of the present disclosure is to provide an estimation device or the like that can suppress deterioration in an accuracy for estimating a line of sight or a face orientation in an image of a person due to a state of the image.

Solution to Problem

An estimation device according to one aspect of the present disclosure includes: perturbation means for generating a plurality of extraction regions by adding a perturbation to an extraction region of a partial image determined on the basis of positions of feature points extracted from a face image; estimation means for estimating a plurality of directions of at least one of a face and a line of sight and a reliability of each of the plurality of directions on the basis of a plurality of partial images in the plurality of extraction regions of the face image; and integration means for calculating an integrated direction obtained by integrating the plurality of directions on the basis of the estimated reliability.

An estimation method according to one aspect of the present disclosure includes: generating a plurality of extraction regions by adding a perturbation to an extraction region of a partial image determined on the basis of positions of feature points extracted from a face image; estimating a plurality of directions of at least one of a face and a line of sight and a reliability of each of the plurality of directions on the basis of a plurality of partial images in the plurality of extraction regions of the face image; and calculating an integrated direction obtained by integrating the plurality of directions on the basis of the estimated reliability.

A storage medium according to one aspect of the present disclosure that stores a program causing a computer to execute: perturbation processing of generating a plurality of extraction regions by adding a perturbation to an extraction region of a partial image determined on the basis of positions of feature points extracted from a face image; estimation processing of estimating a plurality of directions of at least one of a face and a line of sight and a reliability of each of the plurality of directions on the basis of a plurality of partial images in the plurality of extraction regions of the face image; and integration processing of calculating an integrated direction obtained by integrating the plurality of directions on the basis of the estimated reliability. One aspect of the present disclosure is also implemented by the program stored in the storage medium described above.

Advantageous Effects of Invention

According to the present disclosure, it is possible to suppress the deterioration in the accuracy for estimating a line of sight or a face orientation in an image of a person due to a state of the image.

EXAMPLE EMBODIMENT

First Example Embodiment

Figure 1:
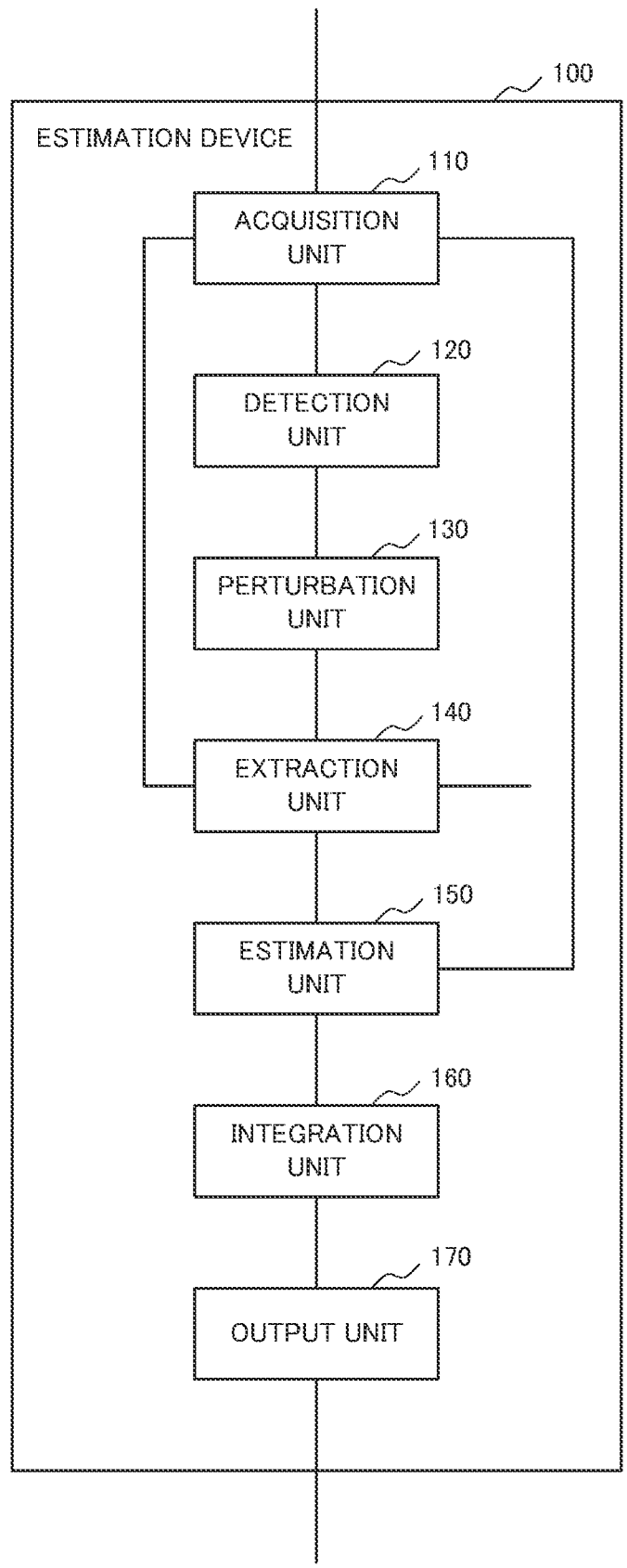
FIG. 1 is a block diagram illustrating an example of a configuration of an estimation device according to a first example embodiment of the present disclosure.

FIG. 1 is a block diagram illustrating a configuration of an estimation device 100 according to a first example embodiment. The estimation device 100 is a device that estimates at least one of a line of sight and a face orientation of a person included in an image. In the description regarding the present example embodiment, a direction of the line of sight of the person and a direction of a face of the person (that is, face orientation described above) are collectively described as a direction of the person. The direction of the line of sight of the person is simply described as a line of sight. Moreover, the direction of the face of the person is simply described as a face orientation. As illustrated in FIG. 1, the estimation device 100 includes an acquisition unit 110, a detection unit 120, a perturbation unit 130, an extraction unit 140, an estimation unit 150, an integration unit 160, and an output unit 170. The estimation device 100 may include other components.

<Acquisition Unit 110>

The acquisition unit 110 acquires image data of an image that includes a face of a person. For example, the acquisition unit 110 may be connected to the estimation device 100 via a communication network and may receive image data from another device that outputs the image data. For example, the acquisition unit 110 may be connected to the estimation device 100 via the communication network and may read the image data from another device that stores the image data. The other device may be an imaging device such as a monitoring camera or a camera built in an electronic device that outputs image data of an imaged image. The other device may be a storage device that stores image data, for example, as a database or the like. The acquisition unit 110 sends the acquired image data to the detection unit 120.

The image data acquired by the acquisition unit 110 is expressed by luminance values of a plurality of pixels. Each of the number of pixels, the number of colors (that is, the number of color components), the number of gradations, or the like included in the image data (in other words, image represented by image data) is not limited to a specific numerical value. The acquisition unit 110 may acquire only image data having a predetermined number of pixels and a predetermined number of colors. The number of pixels and the number of colors of the image data acquired by the acquisition unit 110 are not respectively limited to the specific number of pixels and the specific number of colors. The image data may be still image data or moving image data. For convenience of description, in the following, the image data acquired by the acquisition unit 110 is referred to as an "input image".

In the following description, it is assumed that the input image include a face of one person. In a case where a single input image includes a plurality of faces, it is sufficient that the acquisition unit 110 divide the input image into a plurality of input images each including only one face. It is sufficient that the acquisition unit 110 and other components of the estimation device 100 may perform operations to be described below on each of the plurality of input images generated by the division.

The acquisition unit 110 generates a face image from the acquired input image. The acquisition unit 110 supplies the generated face image to the detection unit 120 and the extraction unit 140. The face image represents an image that includes a part or all of the face of the person. The face image may be an image obtained by removing elements other than the face of the person (for example, background, object, body of person, or the like) from the input image. The face image may be an image obtained by removing elements other than a part of the face of the person from the input image.

The acquisition unit 110 may detect a face region in the input image, for example, using a general method for detecting a face region. The acquisition unit 110 may detect a partial region of the face (for example, region of specific part of face) in the input image using a general method for detecting a region of a specific part (for example, eyes or the like) of the face. Removing the elements other than the face of the person from the input image may be changing pixel values of all the pixels in the region other than the face of the person of the input image to a predetermined pixel value. Removing the elements other than a part of the face of the person from the input image may be changing pixel values of all the pixels in the region other than a part of the face of the person of the input image to a predetermined pixel value. The acquisition unit 110 may change, for example, a pixel value of a pixel in a region other than the detected face region (or partial region of face) to a predetermined pixel value. The acquisition unit 110 may supply an image, of which the pixel value of the pixel in the region other than the detected face region (or partial region of face) is changed to a predetermined pixel value, to the detection unit 120 and the extraction unit 140 as a face image.

(Face Image)

Figure 2:
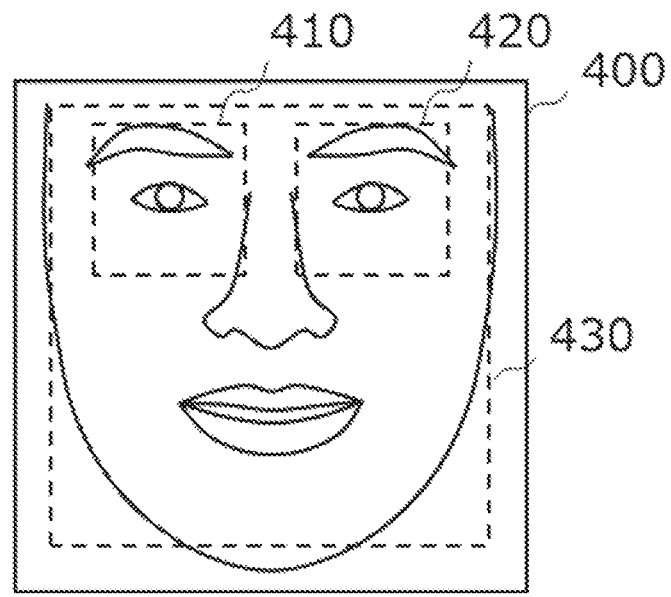
FIG. 2 is a diagram illustrating an example of a face image.

FIG. 2 illustrates an example of the face image (face image 400) generated from the input image by the acquisition unit 110. The face image 400 illustrated in FIG. 2 includes face parts (eyes, eyebrows, nose, and mouth). It is sufficient that the face image include at least information necessary for estimating a line of sight or a face orientation by the estimation unit 150. For example, in a case where the estimation unit 150 estimates a line of sight, only an eye region of the face image is used. Therefore, in a case where the estimation unit 150 estimates a line of sight, it is sufficient that the face image include at least the eyes. In the following description, an image of the eye region is also referred to as an eye region image.

In the description of each example embodiment of the present disclosure, an image generated from the input image by the acquisition unit 110, that is, an image including at least parts of a face extracted from the input image by the acquisition unit 110 is referred to as a face image. An image extracted by the extraction unit 140 from a region of the face image determined on the basis of a position of a feature point detected by the detection unit 120 and a region obtained by adding a perturbation to the region is referred to as a partial image.

In a case where the input image is a moving image, the input image includes a plurality of images (that is, frames). In this case, not all the frames included in the input image include the face. There is a possibility that one frame includes the face and another frame does not include the face. Therefore, in a case where the input image is a moving image, the acquisition unit 110 may extract only an image including the face of the person from the moving image and supply the extracted image to the detection unit 120 and the extraction unit 140 as a face image. With this configuration, processing (to be described later) for estimating the line of sight or the face orientation by the estimation device 100 can be efficiently performed.

In a case where the input image is a still image, the acquisition unit 110 may supply the input image to the detection unit 120 and the extraction unit 140 as a face image. The acquisition unit 110 may process the input image and supply the processed input image to the detection unit 120 and the extraction unit 140 as a face image. In the latter case, for example, the acquisition unit 110 may detect a face of a person in the input image, extract a part of the input image including the detected face as a face image, and supply the extracted face image to the detection unit 120 and the extraction unit 140.

The face image may be a monochrome image. The face image may be a color image. That is, a pixel value of a pixel of the face image indicates values indicating magnitudes of a plurality of color components such as red (R), green (G), blue (B), or the like. In this case, the acquisition unit 110 may convert the face image in such a way that the number of colors in the face image is set to be the predetermined number of colors. The acquisition unit 110 may convert the face image in such a way that the number of gradations in the face image is set to be the predetermined number of gradations. The acquisition unit 110 may supply the converted face image to the detection unit 120 and the extraction unit 140. For example, in a case where the face image is a color image and information regarding a color included in the face image (saturation, hue) is not used, the acquisition unit 110 may convert the face image into a face image expressed by a single-component gray scale. The face image converted in this way is also simply referred to as a "face image" below.

<Detection Unit 120>

The detection unit 120 receives the face image supplied from the acquisition unit 110 (for example, face image 400 illustrated in FIG. 2) and detects feature points of a face from the received face image. The feature points of the face are feature points determined for the face or parts of the face.

In a case where the direction estimated by the estimation device 100 is a direction of a line of sight, the detection unit 120 may detect feature points determined for the eyes. The detection unit 120 may, for example, detect the center of the pupil of the eye from the face image as the feature point. The detection unit 120 may further detect a plurality of points on the outline of the eye as the feature points. The center of the pupil and the plurality of points on the outline of the eye detected by the detection unit 120 as the feature points are referred to as feature points of the eye below.

The plurality of points on the outline of the eye includes, for example, four points including an inner canthus, an outer canthus, a center of an upper eyelid, and a center of a lower eyelid. The inner canthus (so-called inner corner of eye) indicates a point on the inner side of the face of two points, where the upper and the lower eyelids are closed, at both ends of the outline of the eye. The outer canthus (so-called outer corner of eye) indicates a point on the outer side of the face of the two points where the upper and the lower eyelids are closed. The center of the upper eyelid is a point at the center of the border between the upper eyelid and the eyeball in the lateral direction. The center of the lower eyelid is a point at the center of the border between the lower eyelid and the eyeball in the lateral direction.

In the present example embodiment, in the following description, the extraction unit 140 extracts a partial image including the point at the center of the pupil as the center. The extraction unit 140 may extract a partial image including a midpoint of a line segment that connects the inner canthus and the outer canthus as the center, instead of the point at the center of the pupil. The extraction unit 140 may extract a partial image including a point determined on the basis of the four points including the inner canthus, the outer canthus, the center of the upper eyelid, and the center of the lower eyelid as the center. In this way, the position of the partial image extracted by the extraction unit 140 is further stabilized. The point based on the four points described above may be the center of gravity of a rectangle having the four points as vertexes. The point based on the four points described above may be an intersection of a line segment connecting the inner canthus and the outer canthus and a line segment connecting the center of the upper eyelid and the center of the lower eyelid. The point based on the four points described above may be the center of gravity of a parallelogram of which two parallel sides each pass through the inner canthus and the outer canthus and other two parallel sides each pass through the center of the upper eyelid and the center of the lower eyelid. The side passing through the inner canthus and the side passing through the outer canthus may be parallel to an axis, of two axes in the image, having a larger angle with respect to the straight line passing through the inner canthus and the outer canthus. The side passing through the center of the upper eyelid and the side passing through the center of the lower eyelid may be parallel to an axis, of the two axes in the image, having a larger angle with respect to the straight line passing through the center of the upper eyelid and the center of the lower eyelid.

In a case where the direction estimated by the estimation device 100 is the direction of the face, the detection unit 120 may detect feature points of the face without limiting to the feature points determined for the eye. For example, the detection unit 120 may detect a plurality of points determined for the eyebrows, the nose, the mouth, the submandibular region, or the like, in addition to the feature points of the eye described above, from the face image. The plurality of points for the eyes, the eyebrows, the nose, the mouth, and the submandibular region detected by the detection unit 120 in this case is referred to as a feature point of the face below. The feature point of the face in the present example embodiment may be a feature point of the face that is often used in general. The feature point of the face in the present example embodiment may be a point that is appropriately determined on the face by an operator of the estimation device 100, for example. In a case where the estimation device 100 estimates the direction of the line of sight and the direction of the face, the detection unit 120 may detect the feature points of the face.

The detection unit 120 may use any one of various known methods, for example, the method described in PTL 3 to detect the feature points of the eye. Similarly, the detection unit 120 may use any one of various known methods, for example, the method described in PTL 3 to detect the feature points of the face. For example, the detection unit 120 may use general machine learning such as supervised learning. In this case, for example, the detection unit 120 learns features and positions of the eyes, the eyebrows, the noses, the mouths, and the submandibular regions in faces of a plurality of persons using face images of the plurality of persons to which positions of feature points of the eyes, the eyebrows, the noses, the mouths, the submandibular regions, or the like are applied. In other words, the detection unit 120 makes a detector in advance, which outputs positions of feature points of an input face image, perform learning using the face image to which the positions of the feature points are applied. Then, the detection unit 120 detects the feature points from the supplied face image using the detector that has been caused to learn.

The detection unit 120 sends information regarding the feature points detected from the face image (for example, feature points of eye or feature points of face) to the perturbation unit 130 and the extraction unit 140.

<Perturbation Unit 130>

The perturbation unit 130 receives the information regarding the feature points detected by the detection unit 120 (for example, feature points of eye or feature points of face) from the detection unit 120. The perturbation unit 130 calculates an amount of a perturbation (hereinafter, referred to as "perturbation amount") to be added to a region of a partial image extracted by the extraction unit 140 on the basis of the received information regarding the feature points. The calculation of the perturbation amount will be described in detail later.

The region of the partial image extracted from the face image is defined on the basis of the feature points as described above. The perturbation indicates a variation to be applied to a position of a region where a partial image is extracted. The perturbation amount is a value indicating a variation applied to a position of a region where a partial image is extracted. The perturbation unit 130 calculates the variation amount on the basis of the information regarding the feature points. To perturb the region of the partial image indicates to determine another region (in other words, to generate another region) by adding the variation determined on the basis of the perturbation amount to a region defined on the basis of the feature points (hereinafter, also described as original region). The perturbation may be a plurality of variations (for example, a set of plurality of variations). In this case, the perturbation unit 130 calculates the plurality of variation amounts on the basis of the information regarding the feature points. To perturb the region is to determine a plurality of regions (in other words, to generate plurality of regions) by applying the plurality of variations indicating the perturbation to each region. In the following description, in a case where a perturbation is represented by a plurality of variations, there is a case where the perturbation is represented as "the perturbation includes the plurality of variations".

Specifically, the perturbation may be, for example, a change in a position of a region, such as a parallel translation. The parallel translation of the region represents a movement of the region with no change in the size and the direction of the region. In this case, the perturbation amount may be represented by a single two-dimensional vector determined according to the information regarding the feature points.

As described above, the perturbation may be a set of the plurality of variations determined according to the information regarding the feature points. The perturbation unit 130 may determine, for example, a plurality of perturbation amounts using a value p calculated on the basis of the information regarding the feature points. The value p may be, for example, a constant multiple of a distance between predetermined feature points. The value p may be, for example, a constant multiple of a value calculated on the basis of a positional relationship between predetermined feature points.

Specifically, for example, the perturbation may be a set of translations of the position of the region that is determined on the basis of two coordinate axes set for the face image and of which at least one of values of two elements of coordinates increases by p. In this case, the perturbation is represented by three vectors including (p, 0), (0, p), and (p, p). The perturbation unit 130 may determine these three vectors as the perturbation amounts. Then, the extraction unit 140 described later may extract a partial image from three regions obtained by moving the original region, defined by the feature points of the face image, according to the three vectors (p, 0), (0, p), and (p, p) and the original region.

For example, the perturbation may be a set of translations of the position of the region that is determined on the basis of two coordinate axes set for the face image and of which at least one of values of two elements of coordinates increases or decreases by p. In this case, the perturbation is represented by eight vectors including (p, 0), (0, p), (p, p), (−p, 0), (0, −p), (−p, p), (p, −p), and (−p, −p). The perturbation unit 130 may determine these eight vectors as the perturbation amounts. Then, the extraction unit 140 described later may extract partial images from eight regions obtained by moving the original region of the face image according to the eight vectors and the original region. A method for calculating and determining the perturbation amount in a case where the perturbation amount is the parallel translation is not limited to the above method.

The perturbation may be, for example, a variation in a size of a region where a partial image is extracted. The variation in the size may be, for example, enlargement. The variation in the size may be reduction. The variation in the size does not need to be isotropic. For example, a variation in a size within the face image in a certain direction may be different from a variation in a size in another direction.

In a case where the perturbation is a variation in a size of a region, the perturbation amount may represent, for example, a change rate of the size of the region. In a case where the perturbation is, for example a variation in a size of a region for multiplying the size of the region by r, the perturbation amount may be r. In a case where the perturbation is, for example, a variation in a size of a region for multiplying a size in the lateral direction by r1 and multiplying a size in the vertical direction by r2, the perturbation amount may be a vector (r1, r2). In a case where the perturbation is a set of a plurality of sizes of variations with different change rates, the perturbation amount may be a set of change rates.

In a case where the perturbation is a variation in a size of a region, the perturbation amount may be, for example, a change amount of the size of the region. The perturbation may be, for example, a change in a size of a region for increasing a size in the vertical direction by s1 and increasing a size in the lateral direction by s2. In this case, the perturbation amount may be a vector (s1, s2). In a case where the perturbation is a set of a plurality of sizes of variations with different change amounts, the perturbation amount may be a set of vectors indicating the change amounts.

The extraction unit 140 applies a variation having a size indicated by the perturbation amount to a region determined on the basis of the information regarding the feature points and extracts partial images from the region determined on the basis of the information regarding the feature points and a region to which the variation in the size is applied. In a case where the perturbation is a variation in a size of a region, the extraction unit 140 may determine a region so as not to change the center position of the region.

The perturbation may be enlargement or reduction of the extracted partial image. In this case, the perturbation amount may be a value indicating a change amount of the size of the partial image. The perturbation amount may be a value indicating a change rate of the size of the partial image. In this case, the perturbation unit 130 may determine the size of the region generated by adding the perturbation to the region of the partial image according to a method similar to the method for determining the size of the region in a case where the perturbation is the variation in the size of the region where the partial image is extracted. In this case, the extraction unit 140 may generate a partial image obtained by the perturbation by converting the partial image extracted from the region determined on the basis of the feature points into an image having the determined size, for example, by interpolation.

The perturbation may be, for example, rotation of a region where a partial image is extracted. In this case, the perturbation amount may be a magnitude of an angle of the rotation. Then, the perturbation may be a set of rotations in which the region determined on the basis of the feature points is rotated around the center point of the region by an angle indicated by the perturbation amount. For example, in a case where the angle amount is t, the perturbation may be a rotation for rotating the region determined on the basis of the feature points by an angle t and a rotation for rotating the region by an angle −t. In this case, the extraction unit 140 may calculate a pixel value of each pixel of an image extracted from the rotated region by interpolation using the pixel value of the pixel of the face image. The perturbation may be other conversion that can adjust a magnitude of deformation according to a parameter.

The perturbation may be addition of noise, for example, white noise or the like to the face image. In this case, the perturbation amount may be a parameter indicating either one of an intensity or an amount of the added noise. A method for generating the noise to be added may be any one of existing methods for generating noise that can adjust either one of the intensity and the amount of the noise according to the parameter. The perturbation may be smoothing of a face image. In this case, the perturbation amount may be a parameter indicating an intensity of the smoothing. A smoothing method may be any one of smoothing methods that can adjust the intensity according to the parameter. The perturbation may be other processing, on the image, that can adjust the intensity or the like according to the parameter.

The perturbation unit 130 may determine a plurality of perturbation amounts. Specifically, for example, the perturbation amount may be determined on the basis of the information regarding the feature points, and in addition, a value of the other perturbation amount of which the value is between zero and the determined perturbation amount value, for example, by a predetermined method using the determined perturbation amount. The perturbation unit 130 may determine, for example, a value obtained by equally dividing a value between zero and the determined value of the perturbation amount by a predetermined number as the other perturbation amount described above. For example, in a case where the predetermined number is two, the perturbation unit 130 may determine a value obtained by dividing the perturbation amount determined on the basis of the information regarding the feature points by two as the other perturbation amount described above.

In the above description, the variation represented by the perturbation does not include a value indicating a variation that does not change the region, and the extraction unit 140 extracts a partial image from the region determined on the basis of the information regarding the feature points. However, the extraction unit 140 may extract a partial image from the region obtained by adding the variation represented by the perturbation amount to the region determined on the basis of the information regarding the feature points and does not necessarily need to extract a partial image from the region determined on the basis of the information regarding the feature points. In this case, the perturbation unit 130 may set a perturbation amount in such a way that the perturbation amount includes a value indicating a variation that does not change a region. Then, in a case where the perturbation amount includes the value indicating the variation that does not change the region, the extraction unit 140 may extract a partial image from the region determined on the basis of the information regarding the feature points.

The perturbation may be a combination of the perturbations described above. The perturbation represented by the combination of the perturbations is, for example, a perturbation that rotates the position of the region, translates the region, and changes the size of the region. The perturbation represented by the combination of the perturbations is not limited to this example.

Figure 3:
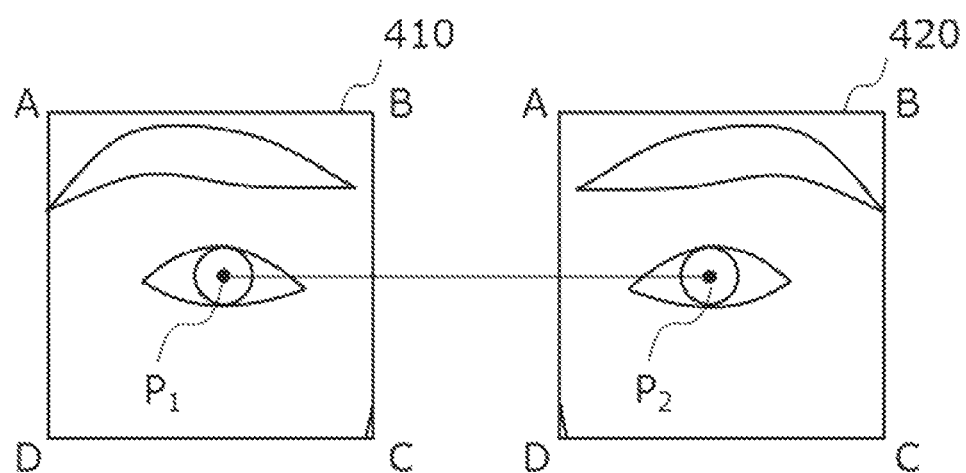
FIG. 3 is a diagram illustrating an example of a partial image (eye region image).
Figure 4:
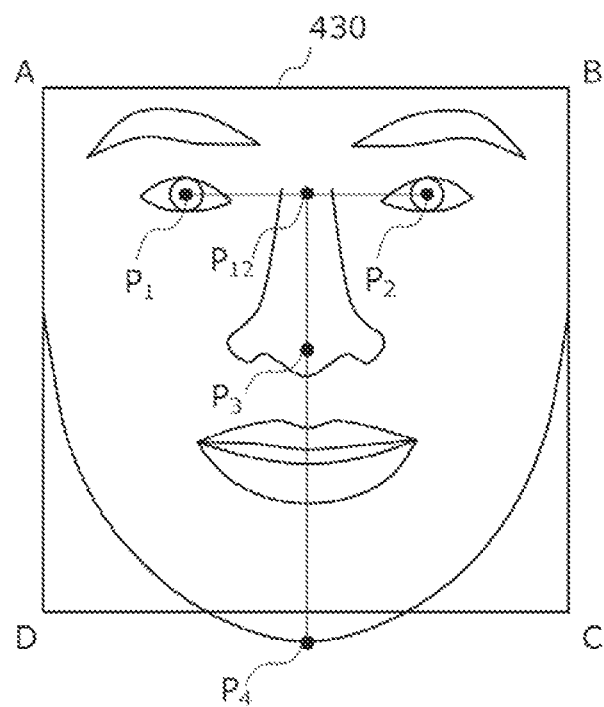
FIG. 4 is a diagram illustrating an example of a partial image (face region image).

Next, an example of a method for determining the perturbation amount will be specifically described with reference to FIGS. 3 and 4. FIGS. 3 and 4 are diagrams illustrating a part of the face image 400 illustrated in FIG. 2 and the feature points detected in the part. A partial image 410 illustrated in FIG. 3 corresponds to the partial image extracted from a region 410 of the face image 400 illustrated in FIG. 2. The region 410 is a region that includes the left eye of the face image 400. A partial image 420 illustrated in FIG. 3 corresponds to a partial image extracted from a region 420 of the face image 400 illustrated in FIG. 2. The region 420 is a region that includes the right eye of the face image 400. A partial image 430 illustrated in FIG. 4 corresponds to a partial image extracted from a region 430 of the face image 400 illustrated in FIG. 2. The partial image 430 corresponds to a partial image extracted from the region 430 including parts of the face such as the eyes and the nose of the face image 400.

The partial image 430 includes a part of the face serving as a clue for estimating a face orientation. For example, a positional relationship between the right eye, the left eye, and the top of the nose in the face image indicates that a distance between the right eye and the nose and a distance between the left eye and the nose generally coincide with each other in the face image in a case where the face faces front. The top of the nose indicates the most protruding portion of the nose. However, in a case where the face faces the right side (that is, in state where person turns one's head to direction of right eye), the distance in the face image between the right eye and the top of the nose is shorter than the distance in the face image between the left eye and the top of the nose. This difference in distance can be used as a clue to estimate that the face faces sideways. The parts of the face included in the partial image 430 are not limited to the right eye, the left eye, and the nose described above.

In the partial images 410 and 420 illustrated in FIG. 3, points $P_1$ and $P_2$ are the centers of the pupils. In the partial image 430 illustrated in FIG. 4, the points $P_1$ and $P_2$ are the centers of the pupils. A point $P_3$ is the top of the nose. A point $P_4$ is the submandibular region. A point $P_{12}$ is a midpoint of a line segment connecting the points $P_1$ and $P_2$.

(Case where Perturbation is Added to Position of Region)

The perturbation unit 130 obtains a perturbation amount indicating a magnitude of a perturbation to be applied to the position of the region of the partial image extracted by the extraction unit 140 on the basis of a value indicating the size of the face (hereinafter, also referred to as size of face). The perturbation unit 130 determines, for example, an interval between the both eyes in the image as the size of the face. Specifically, the perturbation unit 130 may use a distance between the position of the pupil of the right eye (for example, point $P_1$ in partial image 410 in FIG. 3) and the position of the pupil of the left eye (for example, point $P_2$ in partial image 420 in FIG. 3) of the feature points of the eyes detected by the detection unit 120 as the size of the face. In the present example embodiment, the distance is, for example, an Euclidean distance. The distance may be other distances.

The perturbation unit 130 may determine an interval between the midpoint of the both eyes and the lowest point of the jaw as the size of the face. Specifically, the perturbation unit 130 may use a distance between a midpoint of a line segment connecting the position of the pupil of the right eye and the position of the pupil of the left eye (for example, point $P_{12}$ in partial image 430 in FIG. 4) and the lowest point of the jaw (for example, point $P_4$ in partial image 430 in FIG. 4) as the size of the face.

The eye has a characteristic pattern in an image. For example, the white of the eye and the black eye have a clear difference in luminance. Therefore, the feature points of the eyes are often obtained with high accuracy. Therefore, in a case where the interval between the both eyes is used as the size of the face, the size of the face is obtained with high accuracy. In a case where the face faces sideways, the interval between the both eyes in the image (for example, Euclidean distance) is shorter than the interval between the both eyes in a case where the face faces front. In this case, by using the interval between the midpoint of the both eyes and the lowest point of the jaw instead of the interval between the both eyes, it is possible to stably obtain the size of the face regardless of the orientation of the face.

When it is assumed that the size of the face be S, the perturbation unit 130 may obtain a moving amount $d_x$ of the position of the region in the x-axis direction and a moving amount $d_y$ in the y-axis direction indicated by the perturbation as the perturbation amount indicating the magnitude of the perturbation to be added to the position of the partial image, for example, according to the following formula.

Perturbation amount of position $(d_{xi}, d_{yi}) = (u_{xi} \times S, u_{yi} \times S)$ Here, the reference i is a number applied to a variation included in the perturbation, the references $u_{xi}$ and $u_{yi}$ are parameters that is predetermined to determine a magnitude of an i-th variation of the perturbation to be added to the position of the region, and "×" is an operator representing multiplication. $(d_{xi}, d_{yi})$ is a perturbation amount of the position indicating the i-the variation. The parameters $u_{xi}$ and $u_{yi}$ may be the same value. The parameters $u_{xi}$ and $u_{yi}$ may be values different from each other. As described above, the perturbation may include the plurality of variations. Examples of the plurality of parameters in that case are described below.

$(u_{x0}, u_{y0}) = (0.0, 0.0)$ $(u_{x1}, u_{y1}) = (0.1, 0.0)$ $(u_{x2}, u_{y2}) = (0.0, 0.1)$ $(u_{x3}, u_{y3}) = (0.1, 0.1)$

In the above examples, a variation indicated by $(u_{x0}, u_{y0})$ does not change the position of the region where the partial image is extracted.
(Case where Perturbation is Added to Size of Region)

The perturbation unit 130 may obtain, for example, a perturbation amount indicating a perturbation to be added to the size of the partial image extracted by the extraction unit 140 on the basis of the size of the face. The method for calculating the size of the face may be the same as the above-described calculation method. When it is assumed that the size of the face be S, the perturbation unit 130 may obtain a change amount $s_x$ of the size of the region in the x-axis direction and a change amount $s_y$ in the y-axis direction indicated by the perturbation as the perturbation amount indicating the perturbation to be added to the size of the partial image, for example, according to the following formula.

Perturbation amount of size $(s_{xi}, s_{yi}) = (v_{xi} \times S, v_{yi} \times S)$ Here, the perturbation amount of the size $(s_{xi}, s_{yi})$ indicates a magnitude of an i-th variation of the perturbation to be added to the size of the region. The references $v_{xi}$ and $v_{yi}$ are predetermined parameters to determine the magnitude of the i-th variation of the perturbation to be added to the size of the region. The parameters $v_{xi}$ and $v_{yi}$ may be the same value. The parameters $v_{xi}$ and $v_{yi}$ may be values different from each other. As described above, the perturbation may include the plurality of variations. Examples of the plurality of parameters in that case are described below.

$(v_{x0}, v_{y0}) = (0.0, 0.0)$ $(v_{x1}, v_{y1}) = (0.1, 0.0)$ $(v_{x2}, v_{y2}) = (0.0, 0.1)$ $(v_{x3}, v_{y3}) = (0.1, 0.1)$

The parameter $(u_{xi}, u_{yi})$ to determine the size of the perturbation to be added to the position of the region and the parameter $(v_{xi}, v_{yi})$ to determine the magnitude of the perturbation to be added to the size of the region may be predetermined. For example, the perturbation unit 130 may determine these parameters on the basis of properties of the face image 400 or some index.

For example, the perturbation unit 130 may evaluate an image quality of the face image and determine these parameters according to the image quality of the face image. The evaluation of the image quality may be evaluation based on an amount of noise contained in the image. The evaluation of the image quality may be evaluation based on a magnitude of a contrast. The perturbation unit 130 may evaluate the image quality of the face image using any one of existing methods for evaluating image quality. In a case where the image quality of the face image is low, it is considered that an accuracy of the feature points detected by the detection unit 120 is low (in other words, accurate detection fails, and detected position deviates from true position). The perturbation unit 130 may determine the perturbation amount in such a way that the magnitude of the perturbation increases as the image quality of the face image decreases. For example, the perturbation unit 130 may determine the parameter $(u_{xi}, u_{yi})$ to determine the magnitude of the perturbation to be added to the position of the region in such a way that the magnitude of the perturbation increases as the image quality of the face image decreases. The perturbation unit 130 may determine the parameter $(v_{xi}, v_{yi})$ to determine the magnitude of the perturbation to be added to the size of the region in such a way that the magnitude of the perturbation increases as the image quality of the face image decreases. As a result, even in a case where the position of the detected feature point is deviated from the position of the true feature point, a possibility to correctly estimate the orientation of the person increases with any one of the partial images generated by the perturbation.

For example, in a case where the detection unit 120 is configured to detect a face and calculate reliability of the face (for example, detection score) and detect feature points of the detected face, the perturbation unit 130 may determine the above-described parameters to determine the magnitude of the perturbation on the basis of the reliability of the face. Even in a case where the estimation device 100 is configured to receive the position of the detected face and the reliability of the detected face from an external face detection device or the like, the perturbation unit 130 may determine the above-described parameters to determine the magnitude of the perturbation on the basis of the reliability of the face. In a case where the reliability of the detected face is low, there is a high possibility that the accurate position of the face is not detected. In a case where the accurate position of the face is not detected, it is considered that the accuracy of the feature points detected by the detection unit 120 is low. Therefore, as in a case where the image quality of the face image is low, the perturbation unit 130 may determine the above-described parameters (for example, $(u_{xi}, u_{yi})$ and $(v_{xi}, v_{yi})$) on the basis of the reliability of the detected face in such a way as to increase the magnitude of the perturbation.

The perturbation unit 130 sends the calculated perturbation amount (specifically, information regarding perturbation amount) to the extraction unit 140.

<Extraction Unit 140>

The extraction unit 140 receives the face image (illustrated in FIG. 2 as face image 400) from the acquisition unit 110. The extraction unit 140 receives the perturbation amount (specifically, information regarding perturbation amount) from the perturbation unit 130. The extraction unit 140 receives the information regarding the feature points from the detection unit 120.

The extraction unit 140 determines a position of a region on the basis of the received information regarding the feature points and specifies a position of a region where a partial image is extracted on the basis of the position of the region and the received perturbation amount. Specifically, for example, in a case where the perturbation is a change in a range of a region (position change, size change, or the like), the extraction unit 140 extracts a partial image from a region indicated by the position of the region. In a case where the extraction unit 140 is configured to extract the partial image only from the region obtained by adding the perturbation indicated by the perturbation amount to the position of the region based on the information regarding the feature points, it is not necessary to extract the partial image from the position of the region based on the information regarding the feature points. The extraction unit 140 further specifies a region where a partial image is extracted by adding the perturbation indicated by the perturbation amount to the position of the region based on the received information regarding the feature points in the received face image (that is, by applying variation indicated by perturbation amount). Then, the extraction unit 140 extracts the partial image from the specified region of the received face image. For example, in a case where the perturbation is processing such as noise removal or the like on a partial image, the extraction unit 140 may extract a partial image from the position of the region based on the received information regarding the feature points in the received face image and execute processing based on the perturbation amount on the extracted partial image. The extraction unit 140 may execute the processing based on the perturbation amount on the received face image and extract a partial image from the position of the region based on the received information regarding the feature points in the processed face image. The extraction unit 140 extracts the plurality of partial images as described above. In the following description, the processing of extracting the partial image from the region obtained by adding the perturbation to the region determined on the basis of the feature points in the face image is also referred to as normalization processing. The extracted partial image is also referred to as a normalized face image.

In the following, first, an example of an operation for extracting a partial image by the extraction unit 140 in a case where the estimation unit 150 estimates a line of sight will be described. Thereafter, an example of an operation for extracting a partial image by the extraction unit 140 in a case where the estimation unit 150 estimates a face orientation will be described.

(Extraction of Partial Image in Case where Line of Sight is Estimated)

In a case where the estimation unit 150 estimates a line of sight, as described above, the partial images extracted by the extraction unit 140 include an image of a region near the right eye and an image of a region near the left eye (hereinafter, also referred to as eye region image).

The extraction unit 140 first determines four reference coordinates, on the face image, that define the positions and the sizes of the partial images (eye region images of both eyes) using the information regarding the perturbation amount acquired from the perturbation unit 130. In a case where the information regarding the perturbation amount indicating the plurality of variations is acquired from the perturbation unit 130, the extraction unit 140 generates four reference coordinates for each variation indicated by the perturbation amount and extracts partial images (eye region images of right eye and left eye) for each variation indicated by the perturbation amount.

Hereinafter, the above-described four reference coordinates are referred to as reference coordinates A to D. The reference coordinates A to D respectively indicate coordinates of an upper left point, an upper right point, a lower right point, and a lower left point of a partial region. For example, in the partial images 410 and 420 illustrated in FIG. 3 and the partial image 430 illustrated in FIG. 4, at points indicated by the reference coordinates A to D, references A to D are illustrated. Because the reference coordinates A to D are coordinates of a coordinate system defined in a two-dimensional image, each coordinate has a two-dimensional coordinate value. In the following description, it is assumed that coordinate axes of the coordinate system of the image be the x axis and the y axis. In the following description, for example, an x coordinate and a y coordinate of the reference coordinate A are respectively referred to as Ax and Ay.

The extraction unit 140 obtains a reference size of the partial image (that is, size of quadrangle defined by reference coordinates A to D) on the basis of the size of the face. Similarly to the size of the face used to calculate the perturbation amount by the perturbation unit 130, the size of the face may be, for example, the interval between the both eyes (distance between right eye and left eye). Specifically, the extraction unit 140 may use a distance (for example, Euclidean distance) between the position of the pupil of the right eye and the position of the pupil of the left eye of the feature points of the eyes detected by the detection unit 120 as the size of the face.

The size of the face may be the interval between the midpoint of the line segment connecting the both eyes and the lowest point of the jaw. Specifically, the extraction unit 140 may use a distance (for example, Euclidean distance) between the midpoint of the straight line connecting the position of the pupil of the right eye and the position of the pupil of the left eye and the lowest point of the jaw (that is, point in submandibular region) of the feature points of the face detected by the detection unit 120 as the size of the face.

The detection unit 120 detects feature points (for example, feature points of eye, or feature points of face including feature points of eye). The extraction unit 140 can calculate the size of the face using the information regarding the feature points received from the detection unit 120.

Next, the extraction unit 140 calculates a width X0 and a height Y0 of the partial image, for example, according to the following formula (1) to set the reference coordinates A to D.

$$X0 = Y0 = S \times k \quad (1)$$

Here, the reference S represents the size of the face, and the reference k represents a predetermined constant. According to the formula (1), the width X0 and the height Y0 of the partial image are proportional to the size S of the face. The constant k may be appropriately determined. The constant k may be, for example, 0.75. The constant k may be any other value. The formula to calculate X0 and Y0 is not limited to the formula (1).

The extraction unit 140 sets, for example, a rectangular region (square according to calculation in formula (1)) of which the feature point $P_1$ of the center of the pupil of the right eye is the center of gravity and the lengths of two sides are X0 and Y0 as a region where a partial image of the right eye (that is, eye region image) is extracted. The extraction unit 140 sets coordinates of four vertexes of the region as the reference coordinates A to D of the region where the partial image of the right eye is extracted. In a case where a two-dimensional Cartesian coordinate system is defined in the image and two coordinate axes in the coordinate system are the x axis and the y axis, the extraction unit 140 may set, for example, a rectangular region in such a way that a side having the length of X0 is parallel to the x axis and a side having the length of Y0 is parallel to the y axis. The extraction unit 140 similarly sets the region where the partial image of the left eye (that is, eye region image) is extracted with respect to the feature point $P_2$ of the center of the pupil of the left eye. Then, coordinates of four vertexes of the region are set to the reference coordinates A to D of the region where the partial image of the left eye is extracted.

In this case, relative positions between the feature point $P_1$ and the reference coordinates A to D of the region where the partial region of the right eye is extracted is respectively expressed by four vectors (−X0/2, Y0/2), (X0/2, Y0/2), (X0/2, −Y0/2), and (−X0/2, −Y0/2). Similarly, relative positions between the feature point $P_2$ and the reference coordinates A to D of the region where the partial region of the left eye is extracted is respectively expressed by four vectors (−X0/2, Y0/2), (X0/2, Y0/2), (X0/2, −Y0/2), and (−X0/2, −Y0/2).

The extraction unit 140 further adds the perturbation to the region determined on the basis of the information regarding the feature points using the information regarding the perturbation amount received from the perturbation unit 130. Specifically, the extraction unit 140 adds the perturbation to the positions, the sizes, or the like of the reference coordinates A to D using the received information regarding the perturbation amount. In a case where the perturbation is added to the position of the region, the extraction unit 140 adds the perturbation amount of the position $(d_{xi}, d_{yi})$ to each of the reference coordinates A to D. In a case where the received perturbation amount includes the perturbation amounts $(d_{xi}, d_{yi})$ of the plurality of positions as values indicating multiple variations, the extraction unit 140 adds variations indicated by the perturbation amounts of the multiple positions (for example, perturbation amount of position $(d_{xi}, d_{yi})$) to the reference coordinates A to D. Coordinates obtained by adding the variations to the reference coordinates A to D are referred to as perturbated reference coordinates A' to D'. The perturbated reference coordinates A' to D' are also referred to as perturbation reference coordinates A' to D'. Furthermore, an i-th perturbation reference coordinate A' is also referred to as $(A'x_i, A'y_i)$. The perturbation reference coordinates B' to D' are similarly described. Relationships between the perturbation reference coordinates A' to D', the reference coordinates A to D, and the perturbation amount of the position $(d_{xi}, d_{yi})$ are expressed as follows.

$$(A'x_i, A'y_i) = (Ax, Ay) + (d_{xi}, d_{yi})$$

$$(B'x_i, B'y_i) = (Bx, By) + (d_{xi}, d_{yi})$$

$$(C'x_i, C'y_i) = (Cx, Cy) + (d_{xi}, d_{yi})$$

$$(D'x_i, D'y_i) = (Dx, Dy) + (d_{xi}, d_{yi})$$

In a case where the perturbation is added to the size of the region, the extraction unit 140 changes the size of the region by adding the variations to the reference coordinates A to D so as not to move the center of the region. Specifically, the extraction unit 140 adds an amount calculated from the perturbation amount of the size $(s_{xi}, s_{yi})$ to the reference coordinates A to D, for example, as follows. In a case where the perturbation includes the perturbation amount of the size $(d_{xi}, d_{yi})$ as a value indicating a plurality of variations, the extraction unit 140 respectively adds amounts calculated from the perturbation amounts of the plurality of sizes $(d_{xi}, d_{yi})$ to the reference coordinates A to D.

$$(A'x_i, A'y_i) = (Ax, Ay) + (-0.5 \times s_{xi}, -0.5 \times s_{yi})$$

$$(B'x_i, B'y_i) = (Bx, By) + (0.5 \times s_{xi}, -0.5 \times s_{yi})$$

$$(C'x_i, C'y_i) = (Cx, Cy) + (0.5 \times s_{xi}, 0.5 \times s_{yi})$$

$$(D'x_i, D'y_i) = (Dx, Dy) + (-0.5 \times s_{xi}, 0.5 \times s_{yi})$$

The formulas described above indicate that the change in the size of the region made by adding the perturbation to the region is expressed by the perturbation amount of the size $(s_{xi}, s_{yi})$.

The extraction unit 140 may rotate the reference coordinates A to D in such a way that a line segment connecting the center $P_1$ of the pupil of the right eye and the center $P_2$ of the pupil of the left eye is parallel to the two sides of the rectangular (or square) region where the partial image is extracted. Specifically, the extraction unit 140 calculates an angle θ of the line segment connecting the center $P_1$ of the pupil of the right eye and the center $P_2$ of the pupil of the left eye with respect to the horizontal axis of the face image. The extraction unit 140 rotates the reference coordinates A to D of the region including the center $P_1$ of the pupil of the right eye by θ around the center $P_1$ of the pupil of the right eye. The extraction unit 140 further rotates the reference coordinates A to D of the region including the center $P_2$ of the pupil of the left eye by θ around the center $P_2$ of the pupil of the left eye. With this rotation, inclinations of the eyes included in the eye region images are constant regardless of an inclination of the face included in the face image in the horizontal direction.

In a case where the perturbation is a perturbation to be added to the position of the region, the extraction unit 140 may perform the above-described rotation before processing of adding the perturbation to the region. In a case where the perturbation is a perturbation to be added to the size of the region, the extraction unit 140 may perform the above-described rotation after the processing of adding the perturbation to the region. In this case, the extraction unit 140 also rotates the perturbation reference coordinates A' to D'.

Figure 5:
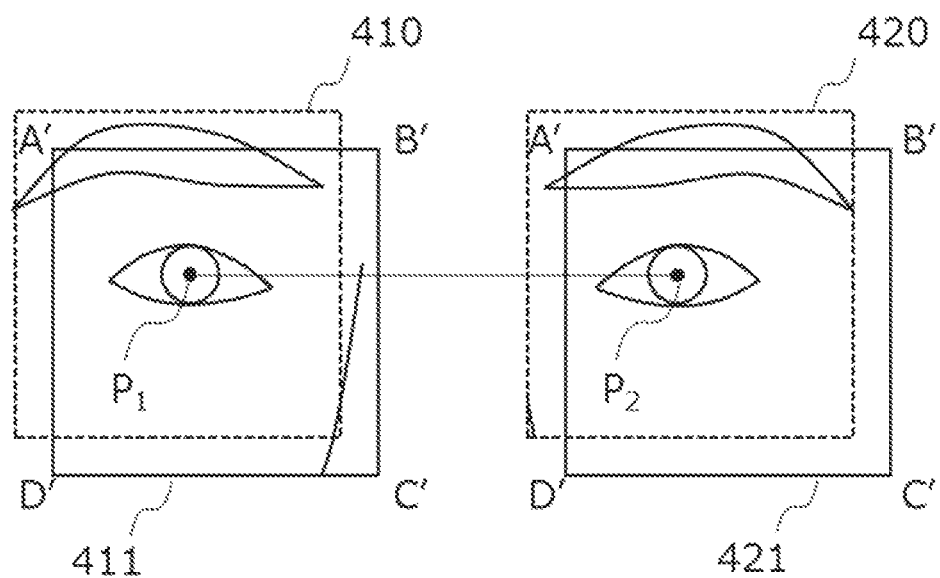
FIG. 5 is a diagram for explaining a flow for extracting a partial image based on a perturbation amount.

FIG. 5 is a diagram schematically illustrating an example of a region obtained by adding a perturbation to a region and a partial image. An example of a partial image (that is, eye region image) generated by the extraction unit 140 will be described with reference to FIG. 5. Partial images 411 and 421 in FIG. 5 indicate partial images extracted from regions generated by adding the perturbations to the regions where the partial images 410 and 420 are extracted. In the example illustrated in FIG. 5, for simplification, only a partial image is illustrated that is extracted from a region in a case where the above-described variation of which the variation number i is three is added. In the example illustrated in FIG. 5, the parameter $(u_{x3}, u_{y3})$ to determine the magnitude of the perturbation to be added to the position of the region is $(u_{x3}, u_{y3}) = (0.08, 0.08)$.

As illustrated in FIG. 5, A' to D' in the partial images 411 and 421 respectively indicate points indicated by the perturbation reference coordinates A' to D'. In a case where the parameter to determine the magnitude of the perturbation to be added to the position of the region is $(u_{x3}, u_{y3})=(0.08, 0.08)$, the perturbation amount of the position $(d_{x3}, d_{y3})$ is $(d_{x3}, d_{y3})=(0.08 \times S, 0.08 \times S)$. As described above, the reference S indicates the size of the face. In the example illustrated in FIG. 5, the reference S indicates the interval between the both eyes (that is, distance between points $P_1$ and $P_2$). In a case where the perturbation is a perturbation to be added to the position of the region, the extraction unit 140 adds the perturbation amount of the position $(d_{x3}, d_{y3})$ to the reference coordinates A to D. Because the size of the face is not negative, $0.08 \times S$ is also not negative. The x and y coordinates of the perturbation reference coordinates A' to D' are values obtained by adding non-negative values to the x and y coordinates of the reference coordinates A to D. Therefore, the region indicated by the perturbation reference coordinates A' to D' corresponds to a region that is obtained by moving the region indicated by the reference coordinates A to D to the lower right direction in the image. The references A' to D' in FIG. 5 indicate this state.

(Extraction of Partial Image in Case where Face Orientation is Estimated)

In a case where the estimation unit 150 estimates a face orientation, the extraction unit 140 extracts an image of a region of an entire face as a partial image. The extraction of the partial image in a case where the face orientation is estimated and the extraction of the partial image in a case where the line of sight is estimated are different from each other in two points, that is, the magnitude of k in the formula (1) and the center position of the reference coordinates A to D.

Specifically, in a case where the estimation unit 150 estimates the face orientation, the constant k in the formula (1) that defines the magnitudes of the reference coordinates A to D may be 2.5, not 0.75 in a case where the line of sight is estimated. The center position of the reference coordinates A to D may be the center position of the face, for example, the top of the nose, not the center of the pupil in a case where the line of sight is estimated.

(Effect in Case where a Plurality of Partial Images is Extracted by Perturbation)

The reference coordinates A to D indicating the region where the extraction unit 140 extracts the partial image are calculated on the basis of the feature points detected by the detection unit 120. For example, in a case where imaging conditions are poor, in a case where a shield exists, and in a case where the image quality of the face image from which the feature points are extracted is low, there is a case where it is not possible for the detection unit 120 to accurately detect the feature points of the face and positions of actual feature points and positions of the detected feature points are deviated from each other. In a case where the positions of the detected feature points are deviated, the position and the size of the region where the partial image is extracted may be different from the position and the size of the region in a case where the positions of the feature points can be accurately detected. In such a case, there is a possibility that parts of the face necessary for estimation of the line of sight or the face orientation are not included in the partial image. There is a possibility that places of the parts of the face necessary for estimation of the line of sight or the face orientation in the partial image are not suitable for estimating the line of sight or the face orientation. In other words, in a case where it is not possible to accurately detect the feature points, it is not necessarily possible to obtain the partial image from which the estimation unit 150 can accurately estimate the line of sight or the face direction. For example, in a case where the line of sight is estimated, it is not necessarily possible for the estimation unit 150 to correctly estimate the line of sight if the position of the eye in the partial image is deviated. Similarly, in a case where it is not possible to accurately detect the feature points, it is not necessarily possible to correctly estimate the face orientation.

In a case where the perturbation in the present example embodiment is added to the region determined on the basis of the detected feature points, a plurality of regions where the partial image is extracted is set around the region determined on the basis of the detected feature points. Even in a case where the feature points are not accurately detected, there is a possibility that any one of the partial images extracted from the region generated by adding the perturbation to the region is an image suitable for estimating the direction of the person (that is, estimation of line of sight or face orientation). If an image suitable for the estimation of the direction of the person is included in the plurality of partial images, the estimation unit 150 which will be described in detail later can accuracy estimate the direction of the person on the basis of the image. In other words, the estimation unit 150 can estimate the direction of the person with a high reliability. The integration unit 160 to be described in detail later integrates the plurality of estimated directions of the person on the basis of the reliability. If the direction of the person with a high reliability is estimated, a possibility increases that the direction of the person obtained by integrating the plurality of estimated directions of the person is a correct direction of the person. In other words, the estimation device 100 according to the present example embodiment can suppress deterioration in the accuracy for estimating the direction of the person caused because the state of the face in the input image is not suitable for the detection of the feature points with high accuracy.

<Estimation Unit 150>

The estimation unit 150 estimates a direction of a person included in a face image (for example, at least one of line of sight of person and face orientation of person). The line of sight indicates a direction to which the person looks. The face orientation indicates a direction in which the face of the person faces. Specifically, the estimation unit 150 estimates a direction of a person on the basis of the plurality of partial images normalized by the extraction unit 140 (that is, plurality of images extracted by extraction unit 140).

In the present example embodiment, when an image of the face is input, the estimation unit 150 estimates the direction of the person using an estimator that is learned in advance in such a way as to estimate the direction of the person on the basis of the input image of the face. A method for learning the estimator may be any one of existing learning methods. For example, the estimation unit 150 causes the estimator to learn in advance a relationship between an appearance of the face in the input image of the face and the line of sight or the face orientation using a plurality of images of the face in which the direction of the person is specified in advance (in other words, image of face including correct answer). The image of the face is, for example, a partial image extracted from a region determined on the basis of the feature points of the face that are given as the correct feature points of the face. The estimation unit 150 estimates the line of sight or the face orientation using the estimator that has performed learning. The estimation unit 150 outputs data of the estimation result to the integration unit 160. In a case of estimating the line of sight, the estimation unit 150 includes an estimator that estimates the line of sight. In a case of estimating the face orientation, the estimation unit 150 includes an estimator that estimates the face orientation. In a case where the line of sight and the face orientation are estimated, the estimation unit 150 includes the estimator that estimates the line of sight and the estimator that estimates the face orientation. In a case where the estimation unit 150 estimates both of the line of sight and the face orientation, the estimation unit 150 may learn in advance the estimator that estimates the direction of the line of sight on the basis of the image of the face and the estimator that estimates the face orientation on the basis of the image of the face. Then, the estimation unit 150 may send the direction of the line of sight estimated by the estimator that estimates the direction of the line of sight on the basis of the image of the face and the face orientation estimated by the estimator that estimates the face orientation on the basis of the image of the face to the integration unit 160.

In the present example embodiment, the direction of the person estimated by the estimator is represented by a vector $(g_x, g_y)$. In the following, first, a vector $(g_x, g_y)$ in a case where the direction of the person estimated by the estimator is a line of sight (that is, a case where estimator estimates line of sight) will be described. Next, a vector $(g_x, g_y)$ in a case where the direction of the person to be estimated is a face orientation (that is, estimator estimates face orientation) will be described. In both cases, the vector $(g_x, g_y)$ is a vector in a coordinate system defined in the image.

(Case where Estimator Estimates Line of Sight)

In a case where the estimator estimates the line of sight, the estimated line of sight is represented by a vector $(g_x, g_y)$. The reference $g_x$ indicates an angle of the line of sight in the horizontal direction, and the reference $g_y$ indicates an angle of the line of sight in the vertical direction. The vector $(g_x, g_y)$ may represent a direction of a deviation of the line of sight with respect to the front of the face. In this case, if the line of sight is directed to the front of the face, $(g_x, g_y)=(0, 0)$ is satisfied. If the line of sight is directed to directly above, $(g_x, g_y)=(0, +90)$ is satisfied. If the line of sight is directed to directly below, $(g_x, g_y)=(0, -90)$ is satisfied. If the line of sight is directed to the right side, $(g_x, g_y)=(-90, 0)$ is satisfied. If the line of sight is directed to the left side, $(g_x, g_y)=(90, 0)$ is satisfied.

The vector $(g_x, g_y)$ may represent a relative direction with respect to the front of the face. In other words, the line of sight may represent a difference between the direction to which the person looks and the direction of the front of the person's face. In this case, the direction to which the eyes of the imaged person look is not specified only according to the vector $(g_x, g_y)$ of the line of sight and is specified according to the vector $(g_x, g_y)$ and the face orientation of the person.

The line of sight estimated by the estimator may use a direction to a camera (that is, direction from eye to camera) as a reference, instead of using the front of the face as a reference. In this case, when the eye looks straight at the camera, that is, when the line of sight coincides with the direction to the camera, the vector is $(g_x, g_y)=(0, 0)$. The vector $(g_x, g_y)$ represents a deviation of the line of sight from the direction to the camera using a horizontal angle and an elevation and depression angle. For example, when the line of sight is directed upward by 30 degrees with respect to the direction to the camera, the vector is $(g_x, g_y)=(0, +30)$. When the direction of the line of sight is directed to the right by 30 degrees with respect to the direction to the camera, the vector is $(g_x, g_y)=(-30, 0)$. When the direction of the line of sight is directed to the left by 30 degrees with respect to the direction to the camera, the vector is $(g_x, g_y)=(30, 0)$.

(Case where Estimator Estimates Face Orientation)

In a case where the estimator estimates the face orientation, in the present example embodiment, the estimated face orientation is represented by a vector $(g_x, g_y)$. The reference $g_x$ indicates an angle of the face orientation in the horizontal direction, and the reference $g_y$ indicates an angle of the face orientation in the vertical direction. The vector $(g_x, g_y)$ may represent an angle of the direction of the front of the face from the reference while setting the direction of the front of the face in a state where the face is oriented straight to the camera (that is, camera is provided in direction of front of face) as a reference. If the face is directly oriented to the camera, $(g_x, g_y)=(0, 0)$ is satisfied. If the face is oriented to directly above, $(g_x, g_y)=(0, +90)$ is satisfied. If the face is oriented to directly below, $(g_x, g_y)=(0, -90)$ is satisfied. If the face is oriented to the right side, $(g_x, g_y)=(-90, 0)$ is satisfied. If the face is oriented to the left side, $(g_x, g_y)=(90, 0)$ is satisfied.

Next, a method for learning the estimator will be described.

(Learning of Estimator)

In the present example embodiment, for example, the estimation unit 150 learns the estimator in advance in such a way as to estimate the direction of the person (for example, line of sight or face orientation) by any one of supervised learning methods. In the following, an example of learning in a case where an angle of a line of sight or a face orientation and its reliability are estimated using Generalized Learning Vector Quantization (GLVQ) as the supervised learning method will be described. The reliability is a value indicating how reliable an angle of a line of sight or a face orientation estimated by the estimator is. The learning method to be used may be a method other than the GLVQ as long as a learning method can estimate the angle of the line of sight or the face orientation and its reliability. For example, a Support Vector Machine (SVM) can be used.

In a case where the estimator is learned, a plurality of combinations of an image of a face in which a direction of a person is specified (that is, partial image) and the specified direction of the person is input to the acquisition unit 110. The acquisition unit 110 sends the plurality of combinations of the image of the face in which the direction of the person is specified and the specified direction of the person to the estimation unit 150.

The estimation unit 150 receives the plurality of combinations of the image of the face in which the direction of the person is specified and the specified direction of the person via the acquisition unit 110. The direction of the person in this case is a correct answer of the direction to be estimated by the estimator (that is, line of sight or face orientation). The direction of the person is represented by a vector $(g_x, g_y)$.

First, the estimation unit 150 classifies continuous "angles" into discrete "classes" by discretizing angles of the direction of the person in the horizontal direction and the vertical direction. Specifically, for example, in a case where the direction of the person is a line of sight, the estimation unit 150 discretizes components of line of sight vectors $(g_x, g_y)$ in the horizontal direction and the vertical direction in a range from −30 degrees to +30 degrees for each 10 degrees. In this case, the line of sight angle in the horizontal direction is divided into six ranges including a range of −30 degrees to −20 degrees, a range of −20 degrees to −10 degrees, a range of −10 degrees to zero degrees, a range of zero degrees to +10 degrees, a range of +10 degrees to +20 degrees, and a range of +20 degrees to +30 degrees. The line of sight angle in the vertical direction is divided into six ranges including a range of −30 degrees to −20 degrees, a range of −20 degrees to −10 degrees, a range of −10 degrees to zero degrees, a range of zero degrees to +10 degrees, a range of +10 degrees to +20 degrees, and a range of +20 degrees to +30 degrees. Regarding the range of the direction of the line of sight of −30 degrees to +30 degrees in the horizontal direction and of −30 degrees to +30 degrees in the vertical direction, the range in the horizontal direction is divided into six ranges, and the range in the vertical direction is divided into six ranges. Therefore, the range of the direction of the line of sight is divided into 6×6=36 ranges. The line of sight is classified into any one of the above-described 36 ranges by discretizing the line of sight represented by the vector ($g_x$, $g_y$) as described above.

Hereinafter, the above-described 36 ranges into which the line of sight is classified are referred to as classes. In the present example embodiment, the estimation unit 150 classifies the direction of the person into any one of 37 classes including the 36 classes and a negative example class related to an image of a region other than the eyes and the face. For example, in a case where the number is smaller as a lower limit value of the range in the vertical direction is smaller and the lower limit value of the range in the vertical direction is the same, the numbers may be applied to the 37 classes in such a way that the number decreases as a number of a lower limit value of the range in the horizontal direction is smaller. For example, a number of one may be assigned to a class of which a range in the horizontal direction is from −30 degrees to −20 degrees and a range in the vertical direction is from −30 degrees to −20 degrees. A number of two may be assigned to a class of which a range in the horizontal direction is from −20 degrees to −10 degrees and a range in the vertical direction is from −30 degrees to −20 degrees.

For example, the vector ($g_x$, $g_y$) is (−15, −15), a class into which the vector is classified is a class of which the range in the horizontal direction is from −20 degrees to −10 degrees and the range in the vertical direction is from −20 degrees to −10 degrees. The number eight is assigned to the class. The number assigned to the negative example class is, for example, zero.

The reason why the negative example class is added is, for example, to learn the estimator in such a way that the estimator outputs information indicating that the partial image is not an estimation target, instead of outputting the direction, in a case where the partial image extracted from the region other than the face is input to the estimator. For example, in a case where the detection unit 120 fails to detect the feature points of the face, there is a case where the partial image extracted from the region other than the face is input to the estimator. In such a case, if there is no negative example class, the estimator classifies the input partial image into any one of the 36 classes. In a case where the estimator performs learning in such a way as to classify images into any one of the classes including the negative example class that indicates that the partial image is not an image of the face (that is, not estimation target of estimator), the estimator can output information indicating that the partial image is not an estimation target in the case described above.

Next, the estimation unit 150 makes the estimator perform learning by learning a relationship between the partial image normalized by the extraction unit 140 and a class into which a direction of a person in the partial image is classified, for example, using the Generalized Learning Vector Quantization (GLVQ). Specifically, the estimation unit 150 learns a multi-class classification problem of 37 classes by the GLVQ. More specifically, the estimation unit 150 calculates an image feature amount f from a partial image (that is, image of face in which correct direction of person is given). The image feature amount f is represented by a vector. The estimation unit 150 adjusts a reference vector m in such a way as to optimize an evaluation value $J_k$ that is calculated from the calculated image feature amount f and the reference vector m according to the formula (2). Specifically, as described later, the estimation unit 150 adjusts the reference vector m, for example, in such a way that the value of the evaluation value $J_k$ approaches −1.

[Expression 1]

$$J_k = \frac{d(f, m_{ki}) - d(f, m_{lj})}{d(f, m_{ki}) + d(f, m_{lj})} \quad (2)$$

Here, a function d (x, y) is a function used to calculate a distance (for example, Euclidean distance or the like) between a vector x and a vector y.

In the following description, it is assumed that M reference vectors m exist in each class. That is, the number of reference vectors is M for each of the 37 classes, and the total number of reference vectors is 37× M. However, the number of reference vectors for each class does not need to be the same. In the present example embodiment, a case will be described where the number of reference vectors is common in each class and is M.

A reference vector $m_{ki}$ in the formula (2) indicates a reference vector having a shortest distance to the image feature amount f, that is, a reference vector closest to the image feature amount f among all the reference vectors determined according to the GLVQ. A class to which the reference vector closest to the image feature amount f belongs is indicated by k. The reference vector $m_{ki}$ indicates an i-th reference vector of M reference vectors belonging to the class k. A reference vector $m_{lj}$ in the formula (2) indicates a reference vector that is the next closest to f except for the M reference vectors belonging to the class k. The reference vector $m_{lj}$ indicates a j-th reference vector of M reference vectors belonging to a class l.

The image feature amount f indicates a direction and a magnitude of a change in luminance in the partial image with a predetermined number of dimensions (for example, several hundreds to thousands). In one example, the image feature amount f indicates an image feature amount f regarding a luminance gradient of an image. As the image feature amount f regarding the luminance gradient, for example, Histograms of Oriented Gradients (HOG) is known. The image feature amount f is represented by a column vector having a predetermined number of elements.

The reference vectors $m_{ki}$ and $m_{lj}$ are column vectors. The number of elements of each of the reference vectors $m_{ki}$ and $m_{lj}$ is the same as the number of elements of the image feature amount f. Therefore, the estimation unit 150 can calculate a distance between the image feature amount f and each of the reference vectors $m_{ki}$ and $m_{lj}$.

The evaluation value $J_k$ in the formula (2) is referred to as a classification error scale in the GLVQ. In the formula (2), the evaluation value $J_k$ satisfies $-1 \le J_k \le +1$. As the evaluation value $J_k$ approaches −1, the evaluation value $J_k$ indicates that an accuracy that the image feature amount f belongs to the class k is high.

The estimation unit 150 determines an optimum reference vector m by the supervised learning using the GLVQ. The determined reference vector m is used when the estimator estimates an angle. The learning of the estimator described above may be, for example, the determination of the reference vector m. A method for estimating an angle by the estimator may be, for example, a method according to "coarse angle estimation" to be described below. The method for estimating an angle by the estimator may be, for example, a method according to "detailed angle estimation" to be described below.

(Coarse Angle Estimation)

The estimator estimates an angle of a direction of a person (that is, line of sight or face orientation) using the reference vector m determined according to the GLVQ and further estimates a reliability according to the formula (2).

Specifically, the estimator first obtains a reference vector closest to the image feature amount f calculated from the extracted partial image, from among all the reference vectors determined according to the GLVQ. In a case where the reference vector closest to the image feature amount f is a reference vector $m_{Ki}$ belonging to the class K, an angle of a line of sight or a face orientation of a face image input to the acquisition unit 110 is included in a range of the angle of the class K. For example, in a case where the reference vector closest to the image feature amount f belongs to an eighth class, the direction of the person (that is, line of sight or face orientation) is included in a range that is a range of an angle of the eighth class and of which a range in the horizontal direction is from −20 degrees to −10 degrees and a range in the vertical direction is from −20 degrees to −10 degrees.

The estimator may output an angle of the center in the range of the angle of the class to which the reference vector closest to the image feature amount f belongs as the estimation result. In the above case, the angle of the center in the range from −20 degrees to −10 degrees in the horizontal direction is −15 degrees, and the angle of the center in the range from −20 degrees to −10 degrees in the vertical direction is also −15 degrees. The estimator may set the direction of −15 degrees in the horizontal direction and −15 degrees in the vertical direction as the estimated direction of the person (that is, line of sight or face orientation). In this case, the angle estimated by the estimator is a vector $(g_x, g_y)=(-15, -15)$.

Next, the estimator calculates the evaluation value $J_k$ according to the formula (2). As described above, the evaluation value $J_k$ satisfies $-1 \leq J_k \leq +1$. The estimator may set a value obtained by inverting a sign of the evaluation value $J_k$ as a reliability. In this case, the reliability is $-J_k$. In this case, the reliability is included in a range from −1 to +1. Then, the larger the value of the reliability is, the higher the reliability of the angle of the direction of the person (that is, line of sight or face orientation) estimated by the estimator.

(Detailed Angle Estimation)

The estimator may calculate an evaluation value $J_k$ for each class according to the formula (3) described later using the reference vector m determined according to the GLVQ and estimate a more detailed angle on the basis of the calculated evaluation value $J_k$.

Specifically, the estimator first obtains a reference vector closest to the image feature amount f calculated from the extracted partial image, from among all the reference vectors determined according to the GLVQ. In the following, as an example, it is assumed that the reference vector closest to the image feature amount f be a reference vector that belongs to a k=8th class.

Next, the estimator obtains a reference vector closest to the image feature amount f for each of classes around the class k=8. The classes around the class k may be, for example, nine classes in total, including the class k, that are classes in a 3×3 region around the region of the class k. For example, in a case of k=8, the classes around the eighth class are the eighth class and eight classes of which angle regions are adjacent to the region of the angle of the eighth class. In the example of the present example embodiment, the classes around the eighth class are nine classes in total with k=1, 2, 3, 7, 8, 9, 13, 14, and 15 centered on the eighth class. The estimator obtains a reference vector closest to the image feature amount f for each of the classes. The obtained reference vectors are reference vectors $m_{ki}$ (k=1, 2, 3, 7, 8, 9, 13, 14, 15).

Moreover, the estimator calculates evaluation values of the classes around the eighth class according to the formula (3) using the reference vectors $m_{ki}$ (k=1, 2, 3, 7, 8, 9, 13, 14, 15) described above. The evaluation values to be calculated are evaluation values $J_k$ (k=1, 2, 3, 7, 8, 9, 13, 14, 15) of the nine classes.

[Expression 2]

$$J_k = \frac{d(f, m_{ki}) - d(f, m_{0j})}{d(f, m_{ki}) + d(f, m_{0j})} \quad (3)$$

The formula (3) is different from the formula (2), and each of the second terms of the denominator and the numerator is a distance between the image feature amount f and a reference vector $m_{0j}$. The reference vector $m_{0j}$ is a reference vector of the 0-th class, that is, a reference vector closest to the image feature amount f among the reference vectors belonging to the negative example class related to the image of the region other than the eyes and the face.

Moreover, the estimator calculates a detailed angle of the direction of the person (that is, line of sight or face orientation) and a reliability of the angle from the evaluation values $J_k$ (k=1, 2, 3, 7, 8, 9, 13, 14, 15) of the nine classes calculated according to the formula (3). Specifically, the estimator arranges the evaluation values $J_k$ of the nine classes in three rows and three columns (hereinafter, described as 3×3) according to arrangement of the angle regions of the classes. The estimator regards the evaluation values $J_k$ arranged in the form of 3×3 as a curved surface of the evaluation value, fits a quadric surface to the curved surface of the evaluation value, and obtains an apex of the obtained quadric surface. The estimator estimates an angle indicated by the obtained apex as the detailed direction of the direction of the person (that is, line of sight or face orientation). The estimator further calculates a reliability of the estimated direction of the person (that is, reliability of angle indicated by obtained apex).

The estimation unit 150 estimates the direction of the person and the reliability by the estimator for each extracted partial image and sends the estimated direction of the person and the estimated reliability (specifically, data indicating direction of person and reliability) to the integration unit 160. As described above, the estimation unit 150 may estimate both of the line of sight and the face orientation as the direction of the person. In this case, the estimation unit 150 may separately estimate a reliability of the angle indicating the line of sight and a reliability of the angle indicating the face orientation. Then, the estimation unit 150 sends the reliability of the angle indicating the line of sight and the reliability of the angle indicating the face orientation to the integration unit 160.

<Integration Unit 160>

The integration unit 160 receives the data (hereinafter, referred to as "estimation data") indicating the direction of the person (that is, line of sight or face orientation) and the reliability estimated by the estimation unit 150 from the estimation unit 150. The integration unit 160 integrates the directions of the person included in the received estimation data on the basis of the reliability included in the estimation data. As described above, the direction of the person is represented by an angle. The integration unit 160 may receive both of the direction of the line of sight and the face orientation from the estimation unit 150. In this case, the integration unit 160 separately integrates the direction of the line of sight and the face orientation.

Specifically, the integration unit 160 integrates the direction of the person on the basis of the reliability as follows. The integration unit 160 may specify an angle indicating a direction of a person of which a reliability is higher than a predetermined threshold among the directions of the person (that is, line of sight or face orientation represented by angle) estimated by the estimation unit 150. Then, the integration unit 160 may calculate an average of the specified angles indicating the direction of the person as the integrated angle indicating the direction of the person (that is, line of sight or face orientation).

The integration unit 160 may first, for example, normalize the reliability. Specifically, first, the integration unit 160 may add a value obtained by inverting a sign of a value of the lowest reliability to all the reliabilities in such a way that the value of the lowest reliability is set to be zero. The integration unit 160 may further normalize the reliability by dividing all the reliabilities by a total sum of the reliabilities in such a way that a total sum of the normalized reliabilities is set to be one. Then, the integration unit 160 may assume the normalized reliability as a weight, and calculate a weighted average of the all angles indicating the directions of the person (that is, line of sight or face orientation) as the angle indicating the integrated direction of the person (that is, line of sight or face orientation). Specifically, the integration unit 160 may calculate an angle and a product of the angle for each angle indicating the direction of the person and calculate a total sum of the products.

The integration unit 160 may set an angle indicating the direction of the person with the highest reliability as the integrated angle indicating the direction of the person.

The integration unit 160 sends integrated data indicating the direction of the person (that is, line of sight or face orientation) to the output unit 170.

<Output Unit 170>

The output unit 170 receives the data indicating the line of sight or the face orientation integrated by the integration unit 160 (hereinafter, referred to as "integrated data") from the integration unit 160. The output unit 170 outputs the integrated data. The estimation data is, for example, data indicating the direction of the person (that is, line of sight or face orientation) integrated by the integration unit 160 in accordance with a predetermined format. Specifically, the output unit 170 may output the estimation data, for example, to another device such as a display device. That is, the output unit 170 may supply the estimation data to the other device.

In a case of outputting the integrated data to the display device, the output unit 170 may superimpose a mark indicating the direction of the person on the input image and output the input image on which the mark indicating the direction of the person is superimposed (also referred to as output image) to the display device.

For example, in a case of outputting the integrated data indicating the direction of the line of sight to the display device, the output unit 170 may superimpose, for example, a mark, such as an arrow, indicating the direction of the line of sight on a position based on the center of the extracted pupil in the input image and output the input image on which the mark is superimposed to the display device. The position based on the center of the extracted pupil may be, for example, a midpoint of a line segment connecting the position of the pupil of the right eye and the position of the pupil of the left eye. The position based on the center of the extracted pupil may be, for example, a point that is away from the above-described midpoint by a predetermined distance in the direction of the line of sight. In a case where the above-described mark is an arrow, the output unit 170 may superimpose an arrow starting from the midpoint described above or the point that is away from the midpoint by the predetermined distance in the direction of the line of sight on the input image.

In a case where integrated data indicating the face orientation is output to the display device, the output unit 170 may superimpose a mark, for example, an arrow or the like indicating the face orientation on a position based on the feature points of the face in the input image and output the input image on which the mark is superimposed to the display device. The position based on the feature points of the face may be, for example, the point indicating the top of the nose. The position based on the feature points of the face may be, for example, a point that is away from the point indicating the top of the nose by a predetermined distance in the direction of the face orientation. In a case where the mark is an arrow, the output unit 170 may superimpose, for example, an arrow starting from the position based on the feature points of the face on the input image.

The output unit 170 may superimpose a mark indicating the direction of the line of sight and a mark indicating the face orientation in the integrated data on the input image.

The output unit 170 may write the estimation data to a storage medium included in the estimation device 100 or a storage device communicably connected to the estimation device 100.

Next, an operation of the estimation device 100 will be described. The estimation device 100 having the configuration described above operates, for example, as described below. However, a specific operation of the estimation device 100 is not limited to an example of an operation to be described below.

<Method for Estimating Line of Sight or Face Orientation (Operation Example of Estimation Device 100)>

Figure 6:
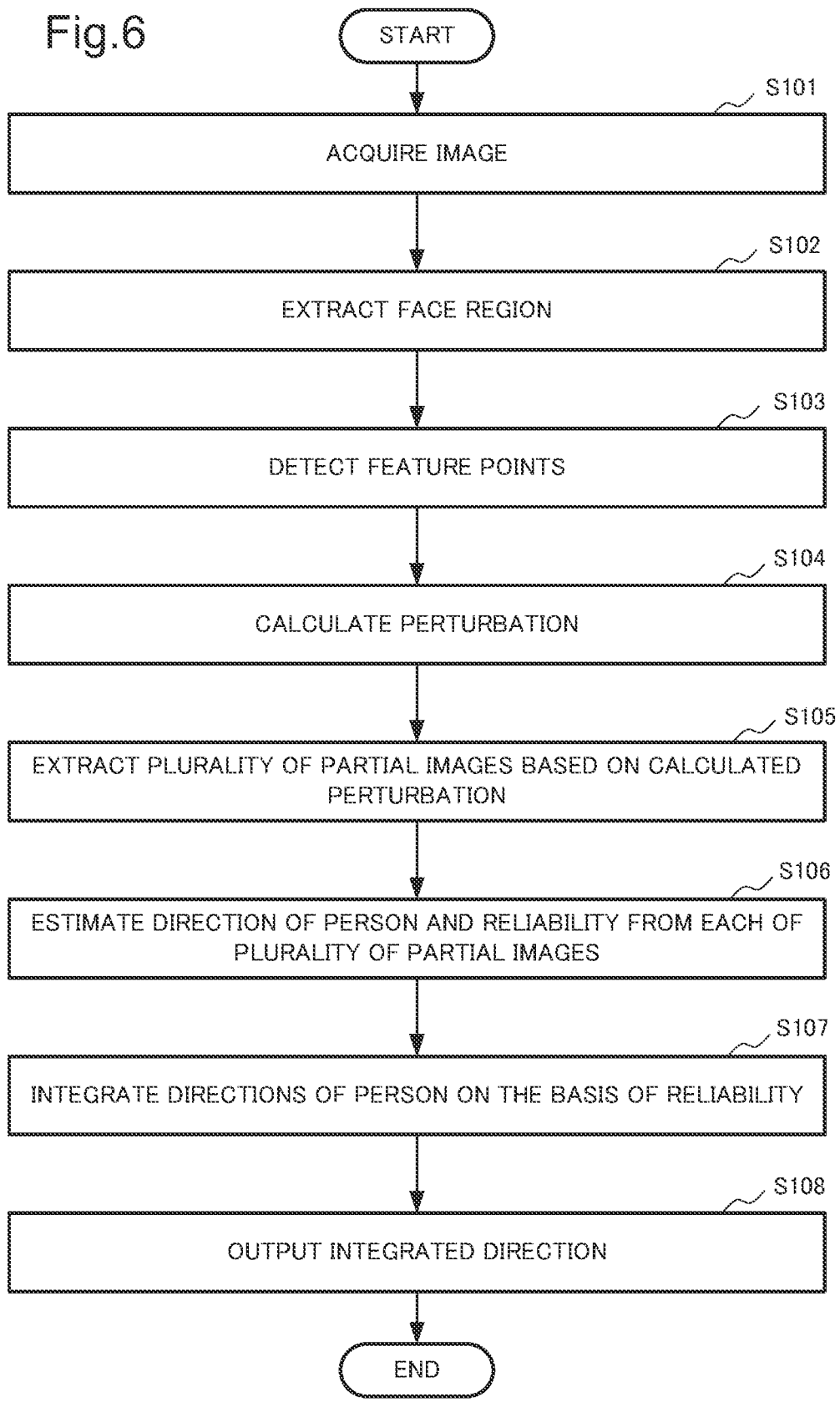
FIG. 6 is a flowchart illustrating an example of an operation of the estimation device according to the first example embodiment of the present disclosure.

FIG. 6 is a flowchart illustrating an example of the operation of the estimation device 100 according to the present example embodiment. In other words, FIG. 6 is a flowchart illustrating an estimation method for estimating the direction of the person (at least one of line of sight and face orientation) executed by the estimation device 100 according to the present example embodiment. The estimation device 100 may, for example, estimate a direction of a person from a face image by sequentially executing processing in each step illustrated in FIG. 6 according to the flow illustrated in FIG. 6.

The estimation device 100 can start the processing illustrated in FIG. 6 at an appropriate timing, for example, a timing designated by a user, a timing when the input image is transmitted from the other device, or the like. In this example, image data input to the estimation device 100 includes a face of a person. The coordinates on the image are represented by a Cartesian coordinate system having a predetermined position (for example, center of image) as an origin.

First, the acquisition unit 110 acquires an input image (step S101).

Next, the acquisition unit 110 extracts a face region from the acquired input image (step S102). The acquisition unit 110 may detect the face region in such a way that a single face region includes a single face. The acquisition unit 110 may extract one or more face regions from the input image. The acquisition unit 110 generates a face image from an image of the extracted face region of the input image. The acquisition unit 110 may generate one or a plurality of face images. Each of the face images includes a face of one person.

The detection unit 120 detects feature points of a part of the face included in the face image generated in step S102 (step S103).

The perturbation unit 130 calculates a magnitude of a perturbation (that is, perturbation amount) to be added to a region (specifically, position or size of region) determined on the basis of the detected feature points using information regarding the feature points of the face calculated in step S103 (step S104). The perturbation amount may include a value indicating a plurality of variations.

The extraction unit 140 extracts a partial image of the face image in the region obtained by adding the perturbation to the region determined on the basis of the detected feature points from the face image generated in step S102 and the perturbation amount calculated in step S104 (step S105). The extraction unit 140 may extract a plurality of partial images including the partial image extracted from the region determined on the basis of the detected feature points. The extraction unit 140 may extract a plurality of partial images obtained by adding the plurality of variations, indicated by the perturbation amount, to the region determined on the basis of the detected feature points, in the face image.

The estimation unit 150 estimates a direction of the person (that is, line of sight or face orientation) and a reliability from each of the plurality of partial images generated in step S105 using the estimator that has performed machine learning in advance (step S106).

The integration unit 160 integrates the directions of the person (that is, line of sight or face orientation) estimated by the estimation unit 150 on the basis of the reliability (step S107).

The output unit 170 outputs estimation data indicating the direction of the person integrated by the integration unit 160 (step S108). The estimation data is visualized, for example, by being output to the display device. The estimation data may be displayed as a numerical value or may be displayed by an arrow, indicating the direction of the line of sight, that is superimposed on the face image.

<Modification>

The first example embodiment can be modified, for example, as the following modification. Two or more modifications to be described later can be appropriately combined.

(Modification 1)

A user may input a position of a feature point such as the center of the right eye, the center of the left eye, or the like and a position of a region where a partial image is extracted. In this case, the estimation device 100 does not need to detect the feature points and does not need to generate the partial image.

(Modification 2)

The shape of the partial image is not necessarily limited to a rectangle. A part of the face (for example, part such as eyebrows that does not directly affect estimation of direction of person) may be excluded from the partial image. A partial image used to estimate the line of sight may be a partial image including both eyes, not a partial image including only one eye (left eye or right eye).

(Modification 3)

The use of the line of sight or the face orientation estimated by the estimation device 100 is not particularly limited. For example, the estimation device 100 may be applied to a system that estimates a line of sight of a person imaged by a monitoring camera installed in a shop and determines a suspicious person from the estimated line of sight.

The estimation device 100 may be applied to a system that estimates a line of sight of a user who faces a screen where information is displayed and estimates interests and concerns of the user on the basis of the estimated line of sight. In addition, the estimation device 100 may be applied to an electronic device that can be operated according to a movement of the line of sight. The estimation device 100 may be applied to driving assistance of an automobile or the like.

(Modification 4)

A specific hardware configuration of the estimation device 100 may variously vary and is not limited to a particular configuration. For example, the estimation device 100 may be implemented using software. The estimation device 100 may be configured in such a way that a plurality of pieces of hardware share a plurality of processes. The configuration of the present modification will be described in detail in the following description regarding the other example embodiment.

<Effects of First Example Embodiment>

The estimation device 100 according to the present example embodiment extracts a plurality of partial images from a plurality of regions obtained by adding a perturbation to a position, a size, or the like of a region where the partial image is extracted. The estimation device 100 estimates a direction of a person (that is, line of sight or face orientation) from the plurality of extracted partial images. The estimation device 100 obtains a result of the estimation of the direction of the person (for example, line of sight or face orientation) by integrating the estimated directions of the person on the basis of a reliability. In this way, the estimation device 100 can stably obtain the robust estimation result by integrating the estimation results on the basis of the plurality of partial images extracted from the region obtained by adding the perturbation to the region according to the reliability.

Second Example Embodiment

Next, a second example embodiment of the present disclosure will be described in detail with reference to the drawings.

<Configuration of Second Example Embodiment>

Figure 7:
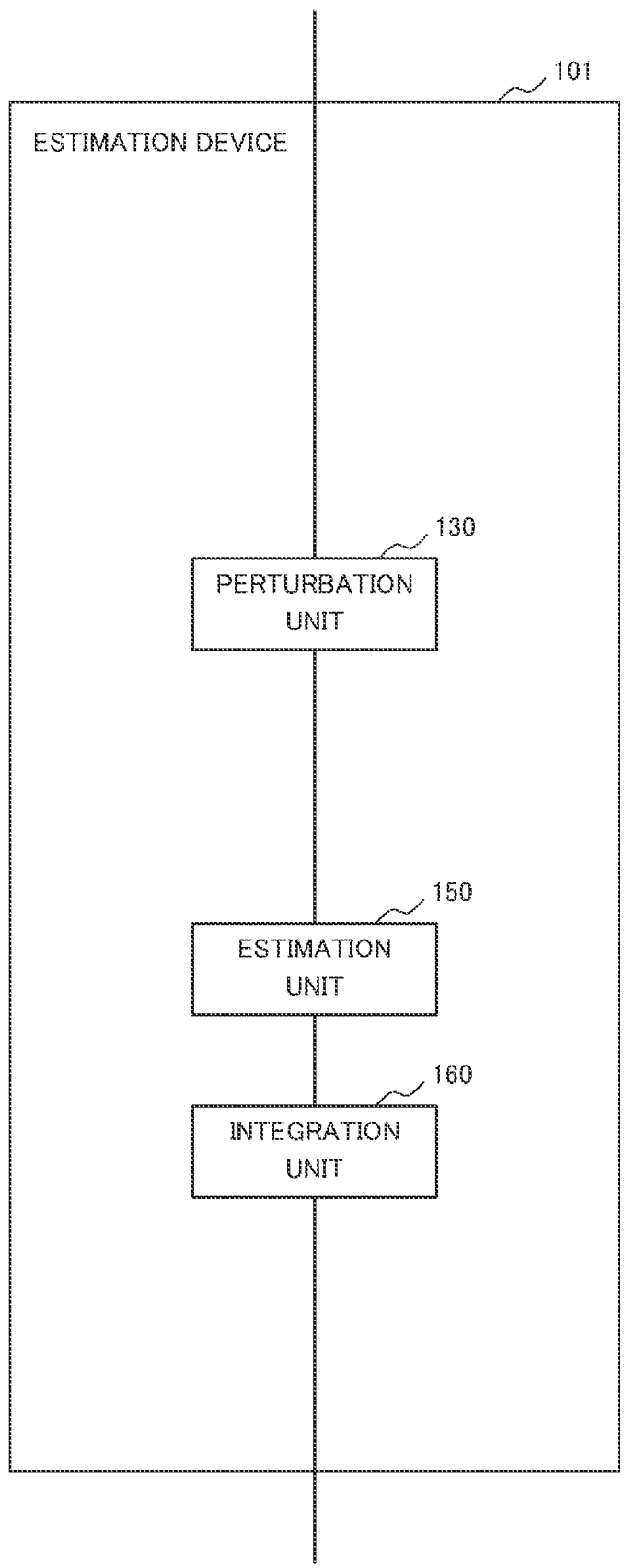
FIG. 7 is a block diagram illustrating an example of a configuration of an estimation device according to a second example embodiment of the present disclosure.

FIG. 7 is a block diagram illustrating an example of a configuration of an estimation device 101 according to the present example embodiment.

As illustrated in FIG. 7, the estimation device 101 according to the present example embodiment includes a perturbation unit 130, an estimation unit 150, and an integration unit 160.

The perturbation unit 130 generates a plurality of extraction regions by adding a perturbation to an extraction region of a partial image determined on the basis of positions of feature points extracted from a face image. The estimation unit 150 estimates a plurality of directions of at least one of a face of a line of sight and a reliability of each of the plurality of directions on the basis of the plurality of partial images in the plurality of extraction regions of the face image. The integration unit 160 calculates an integrated direction obtained by integrating the plurality of directions on the basis of the estimated reliability.

<Operation of Second Example Embodiment>

Figure 8:
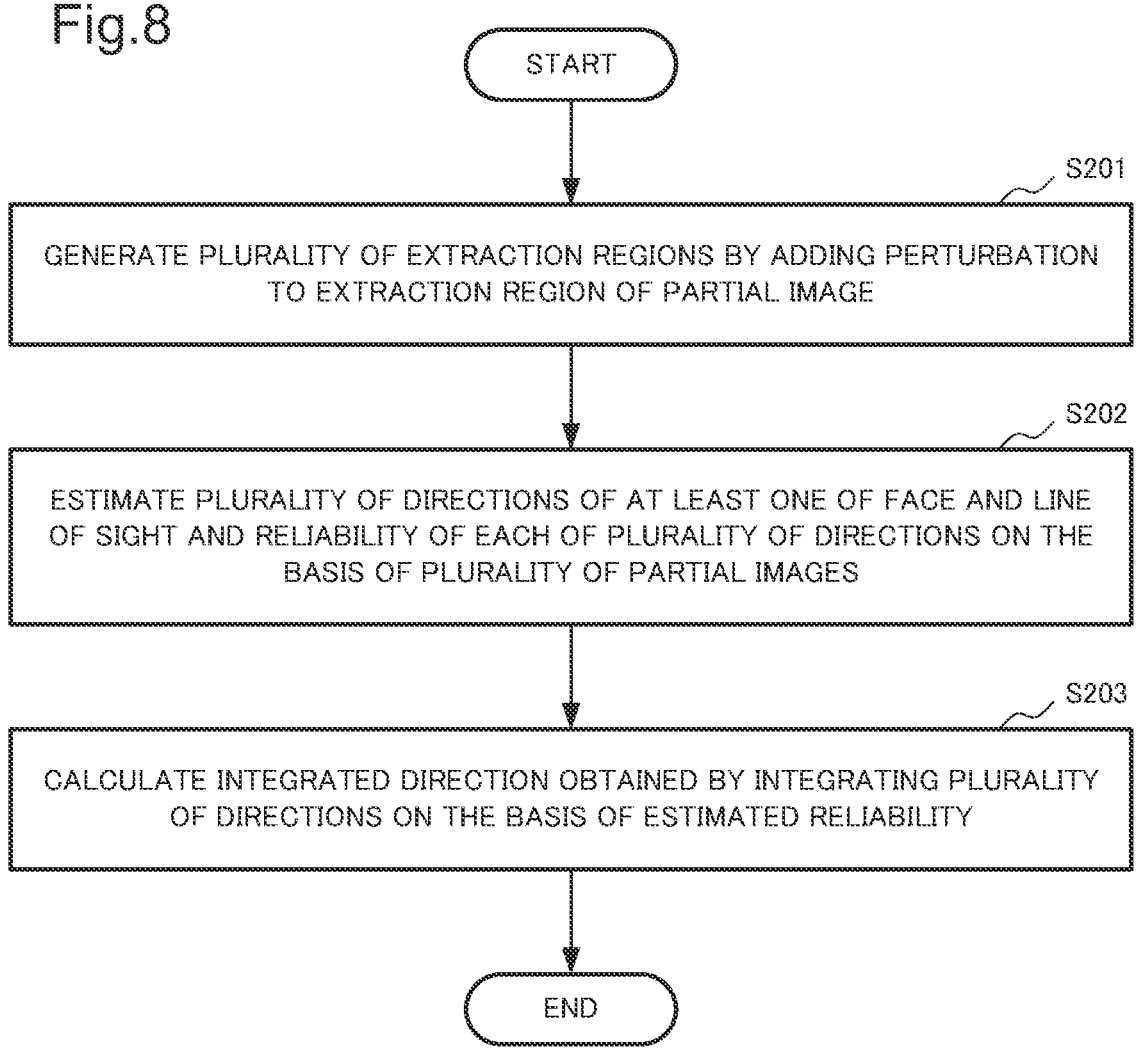
FIG. 8 is a flowchart illustrating an example of an operation of the estimation device according to the second example embodiment of the present disclosure.

FIG. 8 is a flowchart illustrating an example of an operation of the estimation device 101 according to the present example embodiment.

In the operation illustrated in FIG. 8, the perturbation unit 130 generates the plurality of extraction regions by adding the perturbation to the extraction region of the partial image determined on the basis of the positions of the feature points extracted from the face image (step S201). The perturbation unit 130 according to the present example embodiment may operate similarly to the perturbation unit 130 according to the first example embodiment.

The estimation unit 150 estimates the plurality of directions of at least one of the face of the line of sight and the reliability of each of the plurality of directions on the basis of the plurality of partial images in the plurality of extraction regions of the face image (step S202). The estimation unit 150 according to the present example embodiment may estimate the direction and the reliability by an estimator that is made to perform learning in advance in such a way as to estimate the direction and the reliability on the basis of the partial images, similarly to the estimation unit 150 according to the first example embodiment.

Moreover, the integration unit 160 calculates an integrated direction obtained by integrating the plurality of directions on the basis of the estimated reliability (step S203). The integration unit 160 may integrate the plurality of directions on the basis of the reliability by the method similar to that of the integration unit 160 according to the first example embodiment.

<Effect>

The estimation device 101 according to the present example embodiment can suppress deterioration in accuracy for estimating a line of sight or a face orientation in an image of a person due to a state of the image.

This is because the perturbation unit 130 generates the plurality of extraction regions by adding the perturbation to the extraction region of the partial image determined on the basis of positions of feature points extracted from the face image. In addition, this is because the estimation unit 150 estimates the directions and the reliabilities of the directions from the plurality of generated extraction regions. Moreover, the integration unit 160 calculates the integrated direction obtained by integrating the plurality of directions estimated by the estimation unit 150 on the basis of the reliability estimated by the estimation unit 150. In a case where the positions of the feature points extracted from the face image are inaccurate, there is a case where a partial image extracted from an extraction region determined on the basis of the positions is not suitable for the estimation of the direction. Even in such a case, there is a possibility that any one of the partial images of the extraction region obtained by adding the perturbation to the extraction region is suitable for the estimation of the direction. It is expected that the accuracy is higher using the direction obtained by integrating the plurality of directions extracted from the plurality of partial images including the partial image suitable for estimation of the direction on the basis of the reliability of the direction than the accuracy when using the direction extracted from the partial image that is not suitable for estimation of the direction. Therefore, the estimation device 100 can suppress the deterioration in the accuracy for estimating a line of sight or a face orientation in an image of a person due to a state of the image.

Other Example Embodiment

The estimation device 100 according to the first example embodiment can be implemented by a computer that includes a memory to which a program is loaded and a processor that executes the program. The estimation device 100 can be implemented by a plurality of computers communicably connected to each other. The estimation device 100 can be implemented by dedicated hardware. The estimation device 100 can be also implemented by a combination of the above-described computer and dedicated hardware.

Similarly, the estimation device 101 according to the second example embodiment can be implemented by a computer that includes a memory to which a program is loaded and a processor that executes the program. The estimation device 101 can be implemented by a plurality of computers communicably connected to each other. The estimation device 101 can be implemented by dedicated hardware. The estimation device 101 can be also implemented by a combination of the above-described computer and dedicated hardware. More detailed description is made below.

Figure 9:
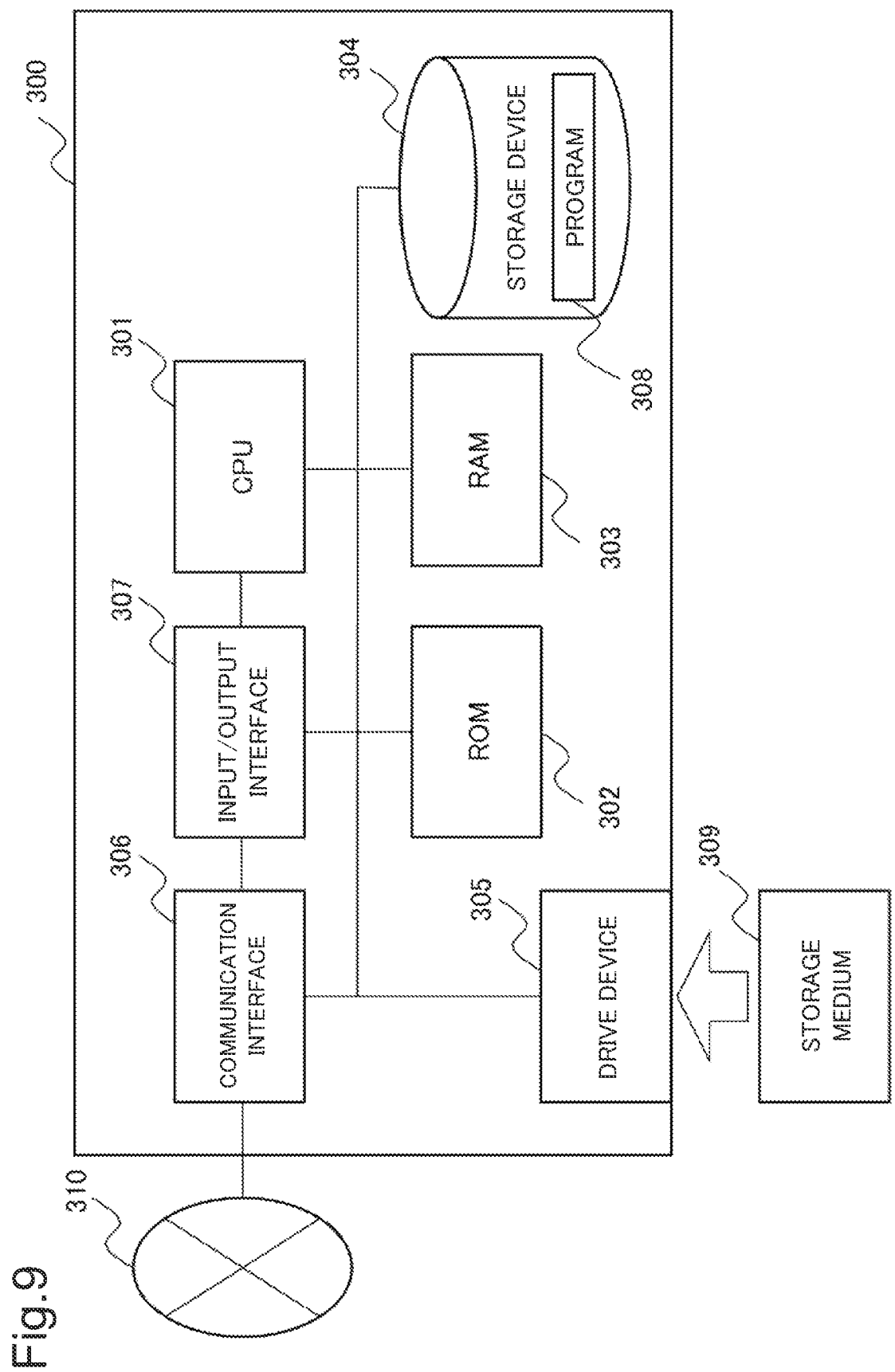
FIG. 9 is a block diagram illustrating an example of a hardware configuration of a computer for implementing an estimation device.

FIG. 9 is a block diagram illustrating an example of a hardware configuration of a computer 300 that can implement the estimation device 100 and the estimation device 101. The computer 300 includes a Central Processing Unit (CPU) 301, a Read Only Memory (ROM) 302, a Random Access Memory (RAM) 303, a storage device 304, a drive device 305, a communication interface 306, and an input/output interface 307.

The CPU 301 executes a program 308 loaded to the RAM 303. The program 308 may be stored in the ROM 302. The program 308 may be recorded in a storage medium 309 such as a memory card and be read by the drive device 305. The program 308 may be transmitted from an external device to the computer 300 via a communication network 310. The communication interface 306 exchanges data with an external device via the communication network 310. The input/output interface 307 exchanges data with peripheral devices (for example, input device, display device, or the like). The communication interface 306 and the input/output interface 307 can function as components that acquire and output data.

The components of the estimation device 100 can be implemented by a processor such as the CPU 301 that executes a program such as the program 308, for implementing the functions of the components of the estimation device 100, loaded to the memory such as the RAM 303. The components of the estimation device 100 are, for example, an acquisition unit 110, a detection unit 120, a perturbation unit 130, an extraction unit 140, an estimation unit 150, an integration unit 160, and an output unit 170.

The components of the estimation device 101 can be implemented by a processor such as the CPU 301 that executes a program such as the program 308, for implementing the functions of the components of the estimation device 101, loaded to the memory such as the RAM 303. The components of the estimation device 100 are, for example, a perturbation unit 130, an estimation unit 150, and an integration unit 160.

The components of the estimation device 100 may be implemented by a single circuit (circuitry) (for example, processor or the like). The components of the estimation device 100 may be implemented by a combination of a plurality of circuits. The circuit and the plurality of circuits may be dedicated circuits or general-purpose circuits. For example, a part of the estimation device 100 may be implemented by a dedicated circuit, and other part may be implemented by a general-purpose circuit.

The components of the estimation device 101 may be implemented by a single circuit (circuitry) (for example, processor or the like). The components of the estimation device 101 may be implemented by a combination of a plurality of circuits. The circuit and the plurality of circuits may be dedicated circuits or general-purpose circuits. For example, a part of the estimation device 101 may be implemented by a dedicated circuit, and other part may be implemented by a general-purpose circuit.

The computer that implements the estimation device 100 and the estimation device 101 does not need to be a single computer. The components of the estimation device 100 and the components of the estimation device 101 may be separately provided in a plurality of computers. For example, the estimation device 100 and the estimation device 100 may be implemented by a plurality of computer devices in cooperation with each other using the cloud computing technology.

Although a part or all of the example embodiments may be described as supplementary notes below, a part or all of the example embodiments are not limited to the following supplementary notes.

(Supplementary Note 1)

An estimation device including:
  perturbation means for generating a plurality of extraction regions by adding a perturbation to an extraction region of a partial image determined based on positions of feature points extracted from a face image;
  estimation means for estimating a plurality of directions of at least one of a face and a line of sight and a reliability of each of the plurality of directions based on a plurality of partial images in the plurality of extraction regions of the face image; and
  integration means for calculating an integrated direction obtained by integrating the plurality of directions based on the estimated reliability.

(Supplementary Note 2)

The estimation device according to supplementary note 1, wherein
  the perturbation means determines, based on the positions of the feature points, the perturbation to be added to the extraction region determined based on the positions of the feature points.

(Supplementary Note 3)

The estimation device according to supplementary note 1 or 2, wherein
  the perturbation means extracts a face region that is a region of the face from the face image, extracts the feature points from the face region, estimates a size of the face based on the positions of the extracted feature points, and determines the perturbation based on the estimated size.

(Supplementary Note 4)

The estimation device according to any one of supplementary notes 1 to 3, wherein
  the perturbation is at least one of a change in a size of the extraction region, a change in a position of the extraction region, a change in an angle of the extraction region, and image processing on a partial image extracted from the extraction region.

(Supplementary Note 5)

The estimation device according to any one of supplementary notes 1 to 4, further including:
  acquisition means for acquiring an input image and extracting the face image from the input image;
  extraction means for extracting the feature points from the face image; and
  output means for outputting the integrated direction.

(Supplementary Note 6)

The estimation device according to supplementary note 5, wherein
  the estimation means estimates a plurality of directions of the face and a plurality of directions of the line of sight,
  the integration means calculates an integrated face direction obtained by integrating the plurality of directions of the face and an integrated line of sight direction obtained by integrating the plurality of directions of the line of sight, and
  the output means superimposes a first mark indicating the integrated face direction and a second mark indicating the integrated line of sight direction on the input image and outputs the input image on which the first mark and the second mark are superimposed.

(Supplementary Note 7)

An estimation method including:
  generating a plurality of extraction regions by adding a perturbation to an extraction region of a partial image determined based on positions of feature points extracted from a face image;
  estimating a plurality of directions of at least one of a face and a line of sight and a reliability of each of the plurality of directions based on a plurality of partial images in the plurality of extraction regions of the face image; and
  calculating an integrated direction obtained by integrating the plurality of directions based on the estimated reliability.

(Supplementary Note 8)

The estimation method according to supplementary note 7, further including
  determining, based on the positions of the feature points, the perturbation to be added to the extraction region determined based on the positions of the feature points is determined.

(Supplementary Note 9)

The estimation method according to supplementary note 7 or 8, further including:
  extracting a face region that is a region of the face from the face image;
  extracting the feature points from the face region;
  estimating a size of the face based on the positions of the extracted feature points; and
  determining the perturbation based on the estimated size.

(Supplementary Note 10)

The estimation method according to any one of supplementary notes 7 to 9, wherein
  the perturbation is at least one of a change in a size of the extraction region, a change in a position of the extraction region, a change in an angle of the extraction region, and image processing on a partial image extracted from the extraction region.

(Supplementary Note 11)

The estimation method according to any one of supplementary notes 7 to 10, further including:
acquiring an input image and extracting the face image from the input image;
extracting the feature points from the face image; and
outputting the integrated direction.

(Supplementary Note 12)

The estimation method according to supplementary note 11, further comprising:
estimating a plurality of directions of the face and a plurality of directions of the line of sight;
calculating an integrated face direction obtained by integrating the plurality of directions of the face and an integrated line of sight direction obtained by integrating the plurality of directions of the line of sight;
superimposing a first mark indicating the integrated face direction and a second mark indicating the integrated line of sight direction on the input image; and
outputting the input image on which the first mark and the second mark are superimposed.

(Supplementary Note 13)

A storage medium that stores a program causing a computer to execute:
perturbation processing of generating a plurality of extraction regions by adding a perturbation to an extraction region of a partial image determined based on positions of feature points extracted from a face image;
estimation processing of estimating a plurality of directions of at least one of a face and a line of sight and a reliability of each of the plurality of directions based on a plurality of partial images in the plurality of extraction regions of the face image; and
integration processing of calculating an integrated direction obtained by integrating the plurality of directions based on the estimated reliability.

(Supplementary Note 14)

The storage medium according to supplementary note 13, wherein
the perturbation processing determines the perturbation to be added to the extraction region determined based on the positions of the feature points, based on the positions of the feature points.

(Supplementary Note 15)

The storage medium according to supplementary note 13 or 14, wherein
the perturbation processing extracts a face region that is a region of the face from the face image, extracts the feature points from the face region, estimates a size of the face based on the positions of the extracted feature points, and determines the perturbation based on the estimated size.

(Supplementary Note 16)

The storage medium according to any one of supplementary notes 13 to 15, wherein
the perturbation is at least one of a change in a size of the extraction region, a change in a position of the extraction region, a change in an angle of the extraction region, and image processing on a partial image extracted from the extraction region.

(Supplementary Note 17)

The storage medium according to any one of supplementary notes 13 to 16, causing a computer to execute:
acquisition processing of acquiring an input image and extracting the face image from the input image;
extraction processing of extracting the feature points from the face image; and
output processing of outputting the integrated direction.

(Supplementary Note 18)

The storage medium according to supplementary note 17, wherein
the estimation processing estimates a plurality of directions of the face and a plurality of directions of the line of sight,
the integration processing calculates an integrated face direction obtained by integrating the plurality of directions of the face and an integrated line of sight direction obtained by integrating the plurality of directions of the line of sight, and
the output processing superimposes a first mark indicating the integrated face direction and a second mark indicating the integrated line of sight direction on the input image and outputs the input image on which the first mark and the second mark are superimposed.

The example embodiments of the present disclosure have been described above. However, the present invention is not limited to these example embodiments. It will be recognized by those of ordinary skill in the art that various changes or example embodiments to which applications are applied may be made therein without departing from the scope of the present invention as defined by the claims. The present invention may include example embodiments in which the matters described herein are appropriately combined or replaced as necessary. For example, the matter described using a specific example embodiment may be applied to the other example embodiment within a consistent range.

REFERENCE SIGNS LIST 100 estimation device
101 estimation device
110 acquisition unit
120 detection unit
130 perturbation unit
140 extraction unit
150 estimation unit
160 integration unit
170 output unit
300 computer
301 CPU
302 ROM
303 RAM
304 storage device
305 drive device
306 communication interface
307 input/output interface
308 program
309 storage medium
310 communication network
400 face image
410 partial image
411 partial image
420 partial image
421 partial image
430 partial image

The invention claimed is:

1. An estimation device comprising:
at least one memory storing instructions; and
at least one processor configured to execute the instructions to:
generate a perturbation extraction region by adding a perturbation to an extraction region in a face image, the perturbation includes a parallel translation of the extraction region, the extraction region being determined based on positions of feature points extracted from the face image, a magnitude of the perturbation being based on an image quality of the face image;

estimate, based on a plurality of partial images including a first partial image and a second partial image, a plurality of directions and a reliability of each of the plurality of directions, the plurality of directions being a plurality of face directions or the plurality of directions of lines of sight, the first partial image being extracted from the extraction region in the face image, the second partial image being extracted from the perturbation extraction region in the face image; and calculate an integrated direction obtained by integrating the plurality of directions based on the estimated reliability, wherein the second partial image is generated by adding a second perturbation to an extracted partial image extracted from the perturbation extraction region in the face image, the second perturbation including enlargement of the extracted partial image, the extracted partial image being a third partial image and a fourth partial image.

2. The estimation device according to claim 1, wherein the image quality is based on a magnitude of a contrast of the face image.

3. The estimation device according to claim 1, wherein the at least one processor is further configured to execute the set of instructions to:
determine, based on the positions of the feature points, the perturbation added to the extraction region determined based on the positions of the feature points.

4. The estimation device according to claim 1, wherein the at least one processor is further configured to execute the set of instructions to:
extract a face region that is a region of the face from the face image; and
extract the feature points from the face region.

5. The estimation device according to claim 1, wherein the at least one processor is further configured to execute the set of instructions to:
acquire an input image and extracting the face image from the input image;
extract the feature points from the face image; and
output the integrated direction.

6. The estimation device according to claim 5, wherein the at least one processor is further configured to execute the set of instructions to:
estimate the plurality of directions of the face and the plurality of directions of the line of sight;
calculate an integrated face direction obtained by integrating the plurality of directions of the face and an integrated line of sight direction obtained by integrating the plurality of directions of the line of sight;
superimpose a first mark indicating the integrated face direction and a second mark indicating the integrated line of sight direction on the input image; and
output the input image on which the first mark and the second mark are superimposed.

7. An estimation method comprising:
generating a perturbation extraction region by adding a perturbation to an extraction region in a face image, the perturbation includes a parallel translation of the extraction region, the extraction region being determined based on positions of feature points extracted from the face image, a magnitude of the perturbation being based on an image quality of the face image;

estimating, based on a plurality of partial images including a first partial image and a second partial image, a plurality of directions and a reliability of each of the plurality of directions, the plurality of directions being a plurality of face directions or the plurality of directions of lines of sight, the first partial image being extracted from the extraction region in the face image, the second partial image being extracted from the perturbation extraction region in the face image; and calculating an integrated direction obtained by integrating the plurality of directions based on the estimated reliability, wherein the second partial image is generated by adding a second perturbation to an extracted partial image extracted from the perturbation extraction region in the face image, the second perturbation including enlargement of the extracted partial image.

8. The estimation method according to claim 7, wherein the image quality is based on a magnitude of a contrast of the face image.

9. The estimation method according to claim 7, further comprising
determining, based on the positions of the feature points, the perturbation added to the extraction region determined based on the positions of the feature points.

10. The estimation method according to claim 7, further comprising:
extracting a face region that is a region of the face from the face image; and
extracting the feature points from the face region.

11. The estimation method according to claim 7, further comprising:
acquiring an input image and extracting the face image from the input image;
extracting the feature points from the face image; and
outputting the integrated direction.

12. The estimation method according to claim 11, further comprising:
estimating the plurality of directions of the face and the plurality of directions of the line of sight;
calculating an integrated face direction obtained by integrating the plurality of directions of the face and an integrated line of sight direction obtained by integrating the plurality of directions of the line of sight;
superimposing a first mark indicating the integrated face direction and a second mark indicating the integrated line of sight direction on the input image; and
outputting the input image on which the first mark and the second mark are superimposed.

13. A non-transitory computer readable storage medium storing a program causing a computer to execute processing of:
generating a perturbation extraction region by adding a perturbation to an extraction region in a face image, the perturbation includes a parallel translation of the extraction region, the extraction region being determined based on positions of feature points extracted from the face image, a magnitude of the perturbation being based on an image quality of the face image;

estimating, based on a plurality of partial images including a first partial image and a second partial image, a plurality of directions and a reliability of each of the plurality of directions, the plurality of directions being a plurality of face directions or the plurality of directions of lines of sight, the first partial image being extracted from the extraction region in the face image, the second partial image being extracted from the perturbation extraction region in the face image; and calculating an integrated direction obtained by integrating the plurality of directions based on the estimated reliability, wherein the second partial image is generated by adding a second perturbation to an extracted partial image extracted from the perturbation extraction region in the face image, the second perturbation including enlargement of the extracted partial image.

14. The storage medium according to claim 13, wherein the image quality is based on a magnitude of a contrast of the face image.

15. The storage medium according to claim 13, wherein the program further causes a computer to execute processing of:
   determining, based on the positions of the feature points, the perturbation added to the extraction region determined based on the positions of the feature points.

16. The storage medium according to claim 13, wherein the program further causes a computer to execute processing of: extracting a face region that is a region of the face from the face image; and extracting the feature points from the face region.

17. The storage medium according to claim 13, wherein the program further causes a computer to execute processing of:
   acquiring an input image and extracting the face image from the input image;
   extracting the feature points from the face image; and
   outputting the integrated direction.

18. The estimation device according to claim 1, wherein the second partial image is generated by adding a second perturbation to an extracted partial image extracted from the perturbation extraction region in the face image, the second perturbation including a rotation of the extracted partial image.

* * * * *